US012579456B2

(12) United States Patent
Alailima et al.

(10) Patent No.: US 12,579,456 B2
(45) Date of Patent: \*Mar. 17, 2026

(54) COGNITIVE PLATFORM FOR DERIVING EFFORT METRIC FOR OPTIMIZING COGNITIVE TREATMENT

(71) Applicant: Akili Interactive Labs, Inc., Boston, MA (US)

(72) Inventors: Titiimaea Alailima, Cambridge, MA (US); Denton J. DeLoss, Riverside, CA (US); Andrew C. Heusser, Newburyport, MA (US); Claudia A. Villena, San Francisco, CA (US)

(73) Assignee: Akili Interactive Labs, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/761,277

(22) Filed: Jul. 1, 2024

(65) Prior Publication Data

US 2025/0005410 A1    Jan. 2, 2025

Related U.S. Application Data

(63) Continuation of application No. 17/890,478, filed on Aug. 18, 2022, now Pat. No. 12,026,636, which is a
(Continued)

(51) Int. Cl.
*G01C 21/36* (2006.01)
*G06F 3/0481* (2022.01)
(Continued)

(52) U.S. Cl.
CPC ............. *G06N 7/01* (2023.01); *G06F 3/0481* (2013.01); *G16H 10/60* (2018.01); *G16H 50/20* (2018.01);
(Continued)

(58) Field of Classification Search
CPC ........ G06N 7/01; G06F 3/0481; G16H 10/60; G16H 50/20; G16H 50/70; G16H 20/70;
(Continued)

(56) References Cited

U.S. PATENT DOCUMENTS 11,129,524 B2 *  9/2021  Ally ....................... A61B 5/162
11,690,560 B2 *  7/2023  Bower ................... A61B 5/162
                                                          600/544

(Continued)

*Primary Examiner* — Kenny Nguyen
(74) *Attorney, Agent, or Firm* — Gregory Finch; Finch Paolino, LLC

(57) ABSTRACT

Adaptive modification and presentment of user interface elements in a computerized therapeutic treatment regimen. Embodiments of the present disclosure provide for non-linear computational analysis of cData and nData derived from user interactions with a mobile electronic device executing an instance of a computerized therapeutic treatment regimen. The cData and nData may be computed according to one or more artificial neural network or deep learning technique to derive patterns between computerized stimuli or interactions and sensor data. Patterns derived from analysis of the cData and nData may be used to define an effort metric associated with user input patterns in response to the computerized stimuli or interactions being indicative of a measure of user engagement or effort. A computational model or rules engine may be applied to adapt, modify, configure or present one or more graphical user interface elements in a subsequent instance of the computerized therapeutic treatment regimen.

16 Claims, 16 Drawing Sheets

Related U.S. Application Data continuation-in-part of application No. 16/653,997, filed on Oct. 15, 2019, now abandoned.

(60) Provisional application No. 62/868,399, filed on Jun. 28, 2019, provisional application No. 62/745,462, filed on Oct. 15, 2018.

(51) Int. Cl.

| | |
|---|---|
| *G06F 3/0482* | (2013.01) |
| *G06N 7/01* | (2023.01) |
| *G08G 1/01* | (2006.01) |
| *G08G 1/0969* | (2006.01) |
| *G16H 10/60* | (2018.01) |
| *G16H 50/20* | (2018.01) |
| *G16H 50/70* | (2018.01) |
| *H04N 7/18* | (2006.01) |
| *A61M 21/00* | (2006.01) |

(52) U.S. Cl.

CPC ..... *G16H 50/70* (2018.01); *A61M 2021/0005* (2013.01); *A61M 2021/0022* (2013.01); *A61M 2205/18* (2013.01)

(58) Field of Classification Search

CPC ........ G16H 40/63; G16H 40/67; G16H 20/10; A61M 2021/0005; A61M 2021/0022; A61M 2205/18; A61M 2021/0027; A61M 2021/005; A61M 2205/332; A61M 2205/3553; A61M 2205/3584; A61M 2205/3592; A61M 2205/505; A61M 2205/52; A61M 2230/005; A61M 2230/04; A61M 2230/06; A61M 2230/10; A61M 2230/205; A61M 2230/30; A61M 2230/50; A61M 2230/65; A61M 21/00

See application file for complete search history.

(56) References Cited

U.S. PATENT DOCUMENTS

| | | | | |
|---|---|---|---|---|
| 2014/0081667 | A1* | 3/2014 | Joao ....................... | G16H 40/63 |
| | | | | 705/3 |
| 2015/0164418 | A1* | 6/2015 | Johnson ................... | A61B 5/16 |
| | | | | 434/236 |
| 2018/0090024 | A1* | 3/2018 | Somers ................... | A63F 13/00 |
| 2018/0286272 | A1* | 10/2018 | McDermott ............ | A63F 13/46 |
| 2019/0252063 | A1* | 8/2019 | Gordon ................. | G16H 10/60 |

* cited by examiner

500

1000

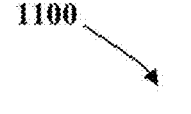
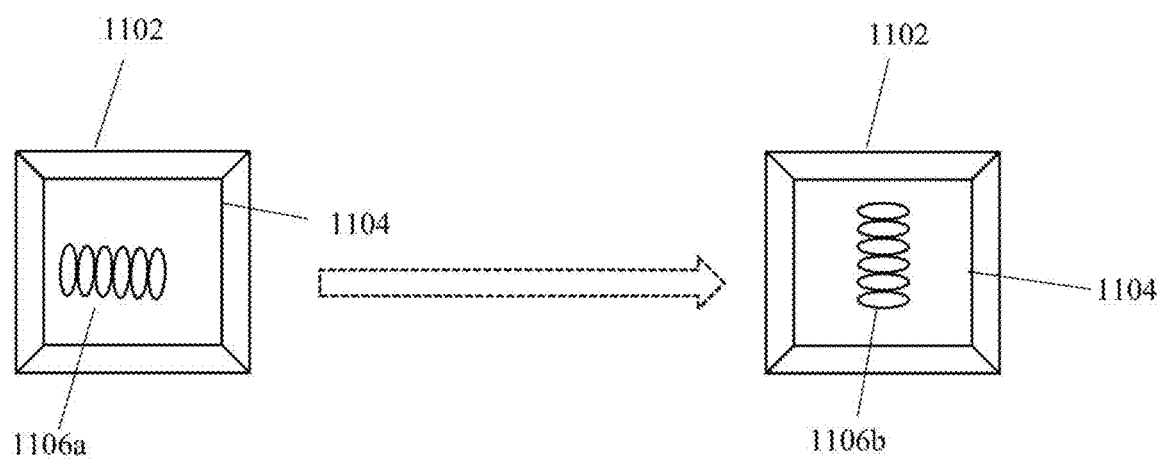
FIG. 6

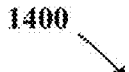

1400

Receive a first plurality of user data from a mobile electronic device, the first plurality of user data comprising user-generated inputs in response to a first instance of one or more computerized stimuli or interactions associated with a computerized therapeutic treatment regimen 1402

Compute the first plurality of user data according to a non-linear computational framework to derive an effort metric based on one or more user response patterns to the computerized stimuli or interaction 1404

Receive a second plurality of user data from the mobile electronic device, the second plurality of user data comprising user-generated inputs in response to a second or subsequent instance of the one or more computerized stimuli or interactions 1406

Compute the second plurality of user data according to the non-linear computational framework to determine a measure of user engagement associated with the second or subsequent instance of the computerized stimuli or interaction based on the effort metric 1408

Modify or deliver at least one user interface element or user prompt to the mobile electronic device in response to the measure of user engagement being below a specified threshold value, the at least one user interface element or user prompt comprising a task or instruction associated with the computerized therapeutic treatment regimen 1410

FIG. 9

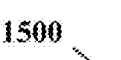

Receive a third or subsequent plurality of user data from the mobile electronic device, the third or subsequent plurality of user data comprising user-generated inputs in response to a third or subsequent instance of the computerized stimuli or interaction comprising the modified user interface element or user prompt
1502

Compute the third or subsequent plurality of user data according to the non-linear computational framework to determine a measure of user engagement associated with a third or subsequent instance of the computerized stimuli or interaction based on the effort metric
1504

Modify or deliver at least one user interface element or user prompt to the mobile electronic device in response to the measure of user engagement being below a specified threshold value, the at least one user interface element or user prompt comprising a task or instruction associated with the computerized therapeutic treatment regimen 1506

Calculate correlation between user engagement data and efficacy metrics 1508

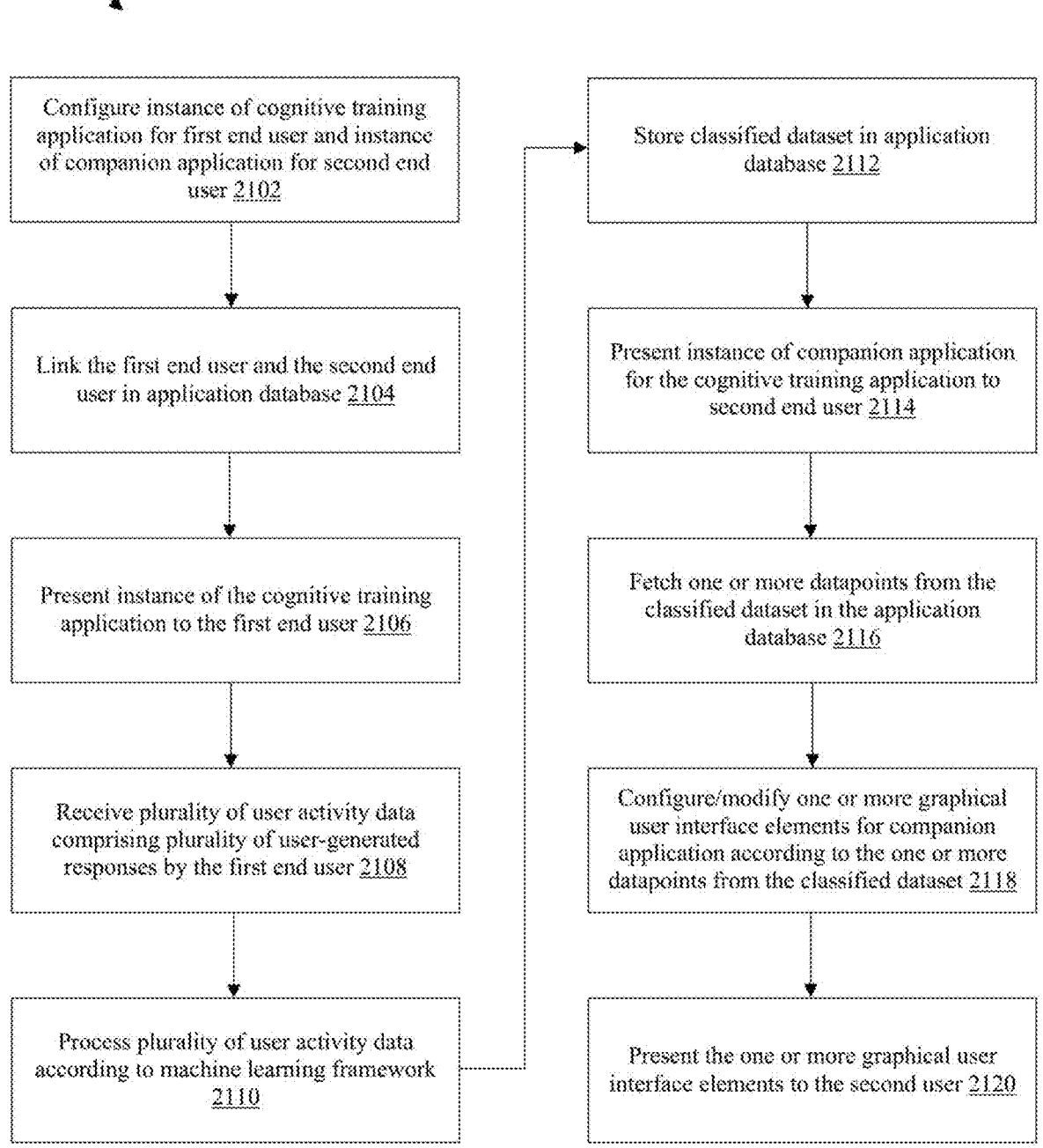

Configure instance of cognitive training application for first end user and instance of companion application for second end user 2102

Link the first end user and the second end user in application database 2104

Present instance of the cognitive training application to the first end user 2106

Receive plurality of user activity data comprising plurality of user-generated responses by the first end user 2108

Process plurality of user activity data according to machine learning framework 2110

Store classified dataset in application database 2112

Present instance of companion application for the cognitive training application to second end user 2114

Fetch one or more datapoints from the classified dataset in the application database 2116

Configure/modify one or more graphical user interface elements for companion application according to the one or more datapoints from the classified dataset 2118

Present the one or more graphical user interface elements to the second user 2120

FIG. 16

COGNITIVE PLATFORM FOR DERIVING EFFORT METRIC FOR OPTIMIZING COGNITIVE TREATMENT

CROSS-REFERENCE TO RELATED APPLICATIONS

This application is a continuation of U.S. application Ser. No. 17/890,478 filed Aug. 18, 2022, which is a continuation-in-part of U.S. application Ser. No. 16/653,997 filed Oct. 15, 2019, which claims priority benefit of U.S. Provisional Application Ser. No. 62/745,462 filed Oct. 15, 2018, and U.S. Provisional Application Ser. No. 62/868,399 filed Jun. 28, 2019, the entireties of each of which being incorporated herein by virtue of this reference.

FIELD

The present disclosure relates to the field of computer-assisted therapeutic treatments; in particular, a cognitive platform for deriving an effort metric for optimizing a computer-assisted therapeutic treatment regimen.

BACKGROUND

A variety of computer-assisted therapeutic treatments have been conceived by the prior art to assist patients in the treatment and management of a broad range of disorders and diseases. In accordance with various prior art teaching, illustrative examples of computer-assisted therapeutic treatments include Web-based and mobile software applications providing one or more user interfaces configured to elicit one or more user behaviors, interactions, and/or responses corresponding with a therapeutic treatment regimen.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Aspects of the present disclosure provide for a system and methods for adaptive modification and presentment of user interface elements in a computerized therapeutic treatment regimen. Certain embodiments provide for non-linear computational analysis of cData and nData derived from user interactions with a mobile electronic device executing an instance of a computerized therapeutic treatment regimen. The cData and nData may be computed according to one or more artificial neural network or deep learning technique, including convolutional neural networks and/or recurrent neural networks, to derive patterns between computerized stimuli or interactions and sensor data. Patterns derived from analysis of the cData and nData may be used to define an effort metric associated with user input patterns in response to the computerized stimuli or interactions being indicative of a measure of user engagement or effort. A computational model or rules engine may be applied to adapt, modify, configure or present one or more graphical user interface elements in a subsequent instance of the computerized therapeutic treatment regimen.

Aspects of the present disclosure provide for a system for adaptively improving user engagement with a computer-assisted therapy, the system comprising a mobile electronic device comprising an input-output device configured to receive a user input and render a graphical output, the input-output device comprising a touch sensor or motion sensor; an integral or remote processor communicatively engaged with the mobile electronic device and configured to provide a graphical user interface to the mobile electronic device, the graphical user interface comprising a computerized stimuli or interaction corresponding to one or more tasks or user prompts in a computerized therapeutic treatment regimen; and a non-transitory computer readable medium having instructions stored thereon that, when executed, cause the processor to perform one or more actions, the one or more actions comprising receiving a plurality of user-generated data corresponding to a plurality of user responses to the one or more tasks or user prompts, the plurality of user-generated data comprising sensor data corresponding to one or more user inputs or device interactions; computing the plurality of user-generated data according to a non-linear computational model to derive an effort metric associated with the computerized therapeutic treatment regimen, the non-linear computational model comprising an artificial neural network; modifying or configuring one or more interface elements of the user interface in response to the effort metric; and computing the plurality of user-generated data in response to modifying or configuring the one or more interface elements to quantify a measure of change in the user-generated data corresponding to the effort metric.

Further aspects of the present disclosure provide for a processor-implemented method for optimizing the efficacy of a computer-assisted therapy, the method comprising receiving, with a processor operably engaged with a database, a first plurality of user data comprising a training dataset, the first plurality of user data comprising at least one user-generated input in response to a first instance of a computerized stimuli or interaction associated with a computerized therapeutic treatment regimen executing on a mobile electronic device; computing, with the processor, the first plurality of user data according to a non-linear computational framework configured to derive an effort metric according to one or more user response patterns to the computerized stimuli or interaction, the non-linear computational framework comprising a convolutional neural network or a recurrent neural network; receiving, with the processor operably engaged with the database, at least a second plurality of user data comprising at least one user-generated input in response to at least a second instance of the computerized stimuli or interaction; computing, with the processor, the second plurality of user data according to the non-linear computational framework to determine a measure of user engagement associated with the second instance of the computerized stimuli or interaction based on the effort metric; modifying or delivering, with the processor operably engaged with the mobile electronic device, at least one user interface element or user prompt associated with the second instance or subsequent instance of the computerized stimuli or interaction in response to the measure of user engagement being below a specified threshold value.

Still further aspects of the present disclosure provide for a non-transitory computer-readable medium encoded with instructions for commanding one or more processors to execute operations of a method for optimizing the efficacy of a computer-assisted therapy, the method comprising receiving a first plurality of user data from a mobile electronic device, the first plurality of user data comprising user-generated inputs in response to a first instance of one or more computerized stimuli or interactions associated with a computerized therapeutic treatment regimen; computing the first plurality of user data according to a non-linear computational framework to derive an effort metric based on one or more user response patterns to the computerized stimuli or interactions, the non-linear computational framework comprising a convolutional neural network or a recurrent neural network; receiving a second plurality of user data from the mobile electronic device, the second plurality of user data comprising user-generated inputs in response to a second or subsequent instance of the one or more computerized stimuli or interactions; computing the second plurality of user data according to the non-linear computational framework to determine a measure of user engagement associated with the second or subsequent instance of the computerized stimuli or interactions based on the effort metric; and modifying or delivering at least one user interface element or user prompt to the mobile electronic device in response to the measure of user engagement being below a specified threshold value, the at least one user interface element or user prompt comprising a task or instruction associated with the computerized therapeutic treatment regimen.

Still further aspects of the present disclosure provide for a computer-implemented method comprising configuring (e.g., with an application server comprising at least one processor) an instance of a cognitive training application for a first end user and an instance of a companion application for the cognitive training application for a second end user; linking (e.g., with the application server) the first end user and the second end user in an application database, wherein linking the first end user and the second end user comprises enabling at least one data transfer interface between the cognitive training application and the companion application; presenting (e.g., with a first end user computing device communicably engaged with the application server) the instance of the cognitive training application to the first end user, wherein the instance of the cognitive training application comprises one or more computerized stimuli or interactions configured to elicit a specified response from the first end user, wherein the specified response comprises a time-varying response deadline; receiving (e.g., with the application server) a plurality of user activity data comprising a plurality of user-generated responses by the first end user to the one or more computerized stimuli or interactions presented during the instance of the cognitive training application; processing (e.g., with the application server) the plurality of user activity data according to a machine learning framework, wherein the machine learning framework comprises an ensemble learning model comprising at least one random decision forest algorithm, wherein the machine learning framework is configured to classify one or more stimulus-response patterns from the plurality of user activity data to generate a classified dataset comprising one or more data labels for one or more attributes of the plurality of user activity data; storing (e.g., with the application server) the classified dataset in the application database; presenting (e.g., with a second end user computing device communicably engaged with the application server) the instance of the companion application for the cognitive training application to the second end user; fetching (e.g., with the instance of the companion application via the application server) one or more datapoints from the classified dataset in the application database; configuring or modifying (e.g., with the instance of the companion application) one or more graphical user interface elements for the companion application according to the one or more datapoints from the classified dataset; and presenting (e.g., with the instance of the companion application) the one or more graphical user interface elements to the second end user, wherein the one or more graphical user interface elements comprise at least one computerized adjustable element configured to provide one or more quantitative metrics for the first end user according to the classified dataset.

In accordance with certain aspects of the present disclosure, the one or more quantitative metrics may comprise a quantified number of sessions of the cognitive training application for the first end user for a specified time period. In certain embodiments, the one or more quantitative metrics may comprise a measure of user engagement for the first end user during the quantified number of sessions. In certain embodiments, the at least one computerized adjustable element is configured to indicate an amount of time the first end user engaged with the first instance of the cognitive training application during the specified time period.

In accordance with certain aspects of the present disclosure, the computer-implemented method may further comprise processing, with the application server, the plurality of user activity data according to the machine learning framework to generate one or more recommendations for the second end user, wherein the one or more recommendations comprise recommendations for improving the measure of user engagement for the first end user. In certain embodiments, the at least one computerized adjustable element may comprise a graphical indication of the quantified number of sessions of the cognitive training application for the first end user and the measure of user engagement for the first end user. The one or more graphical user interface elements may comprise a graphical indication that the measure of user engagement for the first end user is below a specified threshold for the specified time period.

In accordance with certain aspects of the present disclosure, the computer-implemented method may further comprise configuring or modifying, with the application server, the one or more graphical user interface elements for the companion application in response to processing a second or subsequent plurality of user activity data according to the machine learning framework. The computer-implemented method may further comprise providing, with the application server, the one or more quantitative metrics for the first end user to a third end user computing device, wherein the third end user computing device is associated with a third end user comprising a payor user.

Still further aspects of the present disclosure may provide for a computer-implemented system comprising a first end user computing device; a second end user computing device; and an application server communicably engaged with the first end user computing device and the second end user computing device, the application server comprising at least one processor and a non-transitory computer readable medium encoded with one or more processor-executable instructions thereon that, when executed, command the at least one processor to perform one or more operations, the one or more operations comprising configuring an instance of a cognitive training application for a first end user and an instance of a companion application for the cognitive training application for a second end user; linking the first end user and the second end user in an application database, wherein linking the first end user and the second end user comprises enabling at least one data transfer interface between the cognitive training application and the companion application; presenting the instance of the cognitive training application to the first end user, wherein the instance of the cognitive training application comprises one or more computerized stimuli or interactions configured to elicit a specified response from the first end user, wherein the specified response comprises a time-varying response deadline; receiving a plurality of user activity data comprising a plurality of user-generated responses by the first end user to the one or more computerized stimuli or interactions presented during the instance of the cognitive training application; processing the plurality of user activity data according to a machine learning framework, wherein the machine learning framework comprises an ensemble learning model comprising at least one random decision forest algorithm, wherein the machine learning framework is configured to classify one or more stimulus-response patterns from the plurality of user activity data to generate a classified dataset comprising one or more data labels for one or more attributes of the plurality of user activity data; storing the classified dataset in the application database; presenting the instance of the companion application for the cognitive training application to the second end user; fetching, with the instance of the companion application, one or more datapoints from the classified dataset in the application database; configuring or modifying, with the instance of the companion application, one or more graphical user interface elements for the companion application according to the one or more datapoints from the classified dataset; and presenting, with the instance of the companion application, the one or more graphical user interface elements to the second end user, wherein the one or more graphical user interface elements comprise at least one computerized adjustable element configured to provide one or more quantitative metrics for the first end user according to the classified dataset.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The above and other objects, features and advantages of the present disclosure will be more apparent from the following detailed description taken in conjunction with the accompanying drawings, in which:

FIG. 6 is a schematic diagram of an aspect of the cognitive platform of the present disclosure, in accordance with an embodiment;

FIG. 9 is a process flow chart of the cognitive platform of the present disclosure, in accordance with an embodiment;

FIG. 10 is a process flow chart of the cognitive platform of the present disclosure, in accordance with an embodiment;

FIG. 16 is a process flow diagram of a method for configuring a user interface for a companion application within a multi-user cognitive training system, in accordance with certain aspects of the present disclosure.

DETAILED DESCRIPTION

Figure 1:
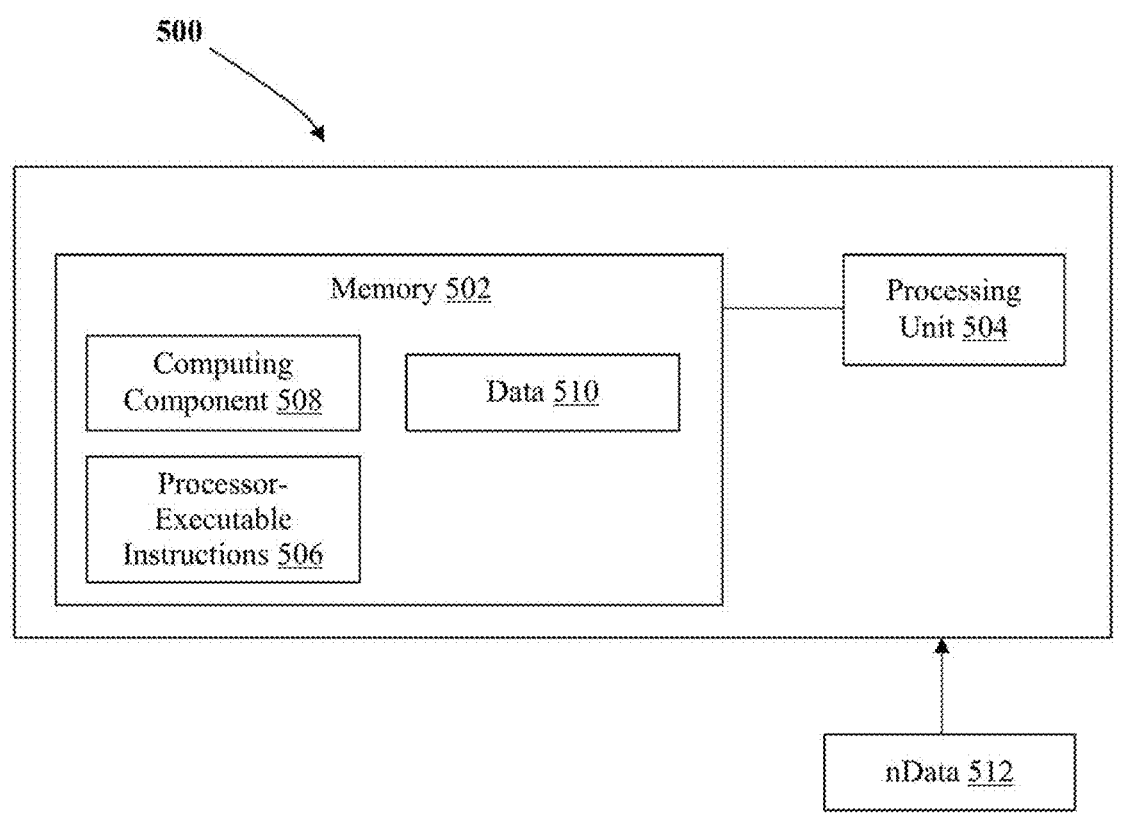
FIG. 1 is a functional block diagram of an exemplary computing device in which one or more aspects of the present disclosure may be implemented.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems comprising a cognitive platform and/or platform product configured for coupling with one or more other types of measurement components, and for analyzing data collected from user interaction with the cognitive platform and/or from at least one measurement of the one or more other types of components. As non-limiting examples, the cognitive platform and/or platform product can be configured for cognitive training and/or for clinical purposes.

In an example implementation, the cognitive platform may be integrated with one or more physiological or monitoring components and/or cognitive testing components.

In another example implementation, the cognitive platform may be separate from, and configured for coupling with, the one or more physiological or monitoring components and/or cognitive testing components.

In any example herein, the cognitive platform and systems including the cognitive platform can be configured to present computerized tasks and platform interactions that inform cognitive assessment (including screening and/or monitoring) or to deliver cognitive treatment.

In any example herein, the platform product herein may be formed as, be based on, or be integrated with, an AKILI® platform product by Akili Interactive Labs, Inc. (Boston, MA), which is configured for presenting computerized tasks and platform interactions that inform cognitive assessment (including screening and/or monitoring) or to deliver cognitive treatment.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The example methods, apparatus and systems comprising the cognitive platform or platform product can be used by an individual, of a clinician, a physician, and/or other medical or healthcare practitioner to provide data that can be used for an assessment of the individual.

In non-limiting examples, the methods, apparatus and systems comprising the cognitive platform or platform product can be configured as a monitoring tool that can be configured to detect differences in cognition between individuals (including children) diagnosed with attention deficit hyperactivity disorder and autism spectrum disorders.

In non-limiting examples, the methods, apparatus and systems comprising the cognitive platform or platform product can be used to determine a predictive model tool for detecting differences in cognition between individuals (including children) diagnosed with Attention Deficit Hyperactivity Disorder and autism spectrum disorders, and/or as a clinical trial tool to aid in the assessment of one or more individuals based on differences in cognition between individuals (including children) diagnosed with Attention Deficit Hyperactivity Disorder and autism spectrum disorders, and/or as a tool to aid in the assessment. The example tools can be built and trained using one or more training datasets obtained from individuals already classified as to cognition.

In non-limiting examples, the methods, apparatus and systems comprising the cognitive platform or platform product can be used to determine a predictive model tool of the presence or likelihood of onset of a neuropsychological deficit or disorder, and/or as a clinical trial tool to aid in the assessment of the presence or likelihood of onset of a neuropsychological deficit or disorder of one or more individuals. The example tools can be built and trained using one or more training datasets obtained from individuals having known neuropsychological deficit or disorder.

As used herein, the term "includes" means includes but is not limited to, the term "including" means including but not limited to. The term "based on" means based at least in part on.

The example platform products and cognitive platforms according to the principles described herein can be applicable to many different types of neuropsychological conditions, such as but not limited to dementia, Parkinson's disease, cerebral amyloid angiopathy, familial amyloid neuropathy, Huntington's disease, or other neurodegenerative condition, autism spectrum disorder (ASD), presence of the 16p11.2 duplication, and/or an executive function disorder (such as but not limited to attention deficit hyperactivity disorder (ADHD), sensory-processing disorder (SPD), mild cognitive impairment (MCI), Alzheimer's disease, multiple sclerosis, schizophrenia, depression, or anxiety).

The instant disclosure is directed to computer-implemented devices formed as example cognitive platforms or platform products configured to implement software and/or other processor-executable instructions for the purpose of measuring data indicative of a user's performance at one or more tasks, to provide a user performance metric. The example performance metric can be used to derive an assessment of a user's cognitive abilities and/or to measure a user's response to a cognitive treatment, and/or to provide data or other quantitative indicia of a user's condition (including physiological condition and/or cognitive condition). In an alternative example, the performance metric can be used to derive an assessment of a user's engagement, attention, adherence to one or more instruction or task, and/or to provide data or other quantitative indicia of a user's attention, engagement, adherence, or response to achieve one or more targeted performance goal. Non-limiting example cognitive platforms or platform products according to the principles herein can be configured to classify an individual as to a neuropsychological condition, including as to differences in cognition between individuals (including children) diagnosed with Attention Deficit Hyperactivity Disorder and autism spectrum disorders, and/or potential efficacy of use of the cognitive platform and/or platform product when the individual is administered a drug, biologic or other pharmaceutical agent, based on the data collected from the individual's interaction with the cognitive platform and/or platform product and/or metrics computed based on the analysis (and associated computations) of that data. Yet other non-limiting example cognitive platforms or platform products according to the principles herein can be configured to classify an individual as to likelihood of onset and/or stage of progression of a neuropsychological condition, including as to a neurodegenerative condition, based on the data collected from the individual's interaction with the cognitive platform and/or platform product and/or metrics computed based on the analysis (and associated computations) of that data. The neurodegenerative condition can be, but is not limited to, Alzheimer's disease, dementia, Parkinson's disease, cerebral amyloid angiopathy, familial amyloid neuropathy, or Huntington's disease.

Any classification of an individual as to likelihood of onset and/or stage of progression of a neurodegenerative condition according to the principles herein can be transmitted as a signal to a medical device, healthcare computing system, or other device, and/or to a medical practitioner, a health practitioner, a physical therapist, a behavioral therapist, a sports medicine practitioner, a pharmacist, or other practitioner, to allow or inform formulation of a course of treatment for the individual or to modify an existing course of treatment, including to determine a change in dosage or delivery regimen of a drug, biologic or other pharmaceutical agent to the individual or to determine an optimal type or combination of drug, biologic or other pharmaceutical agent to the individual.

In any example herein, the platform product or cognitive platform can be configured as any combination of a medical device platform, a monitoring device platform, a screening device platform, or other device platform.

The instant disclosure is also directed to example systems that include platform products and cognitive platforms that are configured for coupling with one or more physiological or monitoring component and/or cognitive testing component. In some examples, the systems include platform products and cognitive platforms that are integrated with the one or more other physiological or monitoring component and/or cognitive testing component. In other examples, the systems include platform products and cognitive platforms that are separately housed from and configured for communicating with the one or more physiological or monitoring component and/or cognitive testing component, to receive data indicative of measurements made using such one or more components.

As used herein, the term "cData" refers to data collected from measures of an interaction of a user with a computer-implemented device formed as a platform product or a cognitive platform.

As used herein, the term "nData" refers to other types of data that can be collected according to the principles herein. Any component used to provide nData is referred to herein as an nData component.

In any example herein, the cData and/or nData can be collected in real-time. In non-limiting examples, the nData can be collected from measurements using one or more physiological or monitoring components and/or cognitive testing components. In any example herein, the one or more physiological components are configured for performing physiological measurements. The physiological measurements provide quantitative measurement data of physiological parameters and/or data that can be used for visualization of physiological structure and/or functions.

In some examples, the nData can be an identification of a type of biologic, drug, or other pharmaceutical agent administered or to be administered to an individual, and/or data collected from measurements of a level of the biologic, drug or other pharmaceutical agent in the tissue or fluid (including blood) of an individual, whether the measurement is made in situ or tissue or fluid (including blood) using collected from the individual. Non-limiting examples of a biologic, drug or other pharmaceutical agent applicable to any example described herein include methylphenidate (MPH), scopolamine, donepezil hydrochloride, rivastigmine tartrate, memantine HCl, solanezumab, aducanumab, and crenezumab.

It is understood that reference to "drug" herein encompasses a drug, a biologic and/or other pharmaceutical agent.

In a non-limiting example, the physiological instrument can be a fMRI, and the nData can be measurement data indicative of the cortical thickness, brain functional activity changes, or other measure.

In other non-limiting examples, nData can include any data that can be used to characterize an individual's status, such as but not limited to age, gender or other similar data.

In any example herein, the data (including cData and nData) is collected with the individual's informed consent.

In any example herein, the one or more physiological components can include any means of measuring physical characteristics of the body and nervous system, including electrical activity, heart rate, blood flow, and oxygenation levels, to provide the nData. This can include camera-based heart rate detection, measurement of galvanic skin response, blood pressure measurement, electroencephalogram, electrocardiogram, magnetic resonance imaging, near-infrared spectroscopy, ultrasound, and/or pupil dilation measures, to provide the nData.

Other examples of physiological measurements to provide nData include, but are not limited to, the measurement of body temperature, heart or other cardiac-related functioning using an electrocardiogramalectrical activity using an electroencephalogram (EEG), event-related potentials (ERPs), functional magnetic resonance imaging (fMRI), blood pressure, electrical potential at a portion of the skin, galvanic skin response (GSR), magneto-encephalogram (MEG), eye-tracking device or other optical detection device including processing units programmed to determine degree of pupillary dilation, functional near-infrared spectroscopy (fNIRS), and/or a positron emission tomography (PET) scanner. An EEG-fMRI or MEG-fMRI measurement allows for simultaneous acquisition of electrophysiology (EEG/MEG) nData and hemodynamic (fMRI) nData.

The fMRI also can be used to provide provides measurement data (nData) indicative of neuronal activation, based on the difference in magnetic properties of oxygenated versus de-oxygenated blood supply to the brain. The fMRI can provide an indirect measure of neuronal activity by measuring regional changes in blood supply, based on a positive correlation between neuronal activity and brain metabolism.

A PET scanner can be used to perform functional imaging to observe metabolic processes and other physiological measures of the body through detection of gamma rays emitted indirectly by a positron-emitting radionuclide (a tracer). The tracer can be introduced into the user's body using a biologically active molecule. Indicators of the metabolic processes and other physiological measures of the body can be derived from the scans, including from computer reconstruction of two- and three-dimensional images of from nData of tracer concentration from the scans. The nData can include measures of the tracer concentration and/or the PET images (such as two- or three-dimensional images).

In any example herein, a task can involve one or more activities that a user is required to engage in. Any one or more of the tasks can be computer-implemented as computerized stimuli or interaction (described in greater detail below). For a targeting task, the cognitive platform may require temporally-specific and/or position-specific responses from a user. For a navigation task, the cognitive platform may require position specific and/or motion-specific responses from the user. For a facial expression recognition or object recognition task, the cognitive platform may require temporally specific and/or position-specific responses from the user. The multi-tasking tasks can include any combination of two or more tasks. In non-limiting examples, the user response to tasks, such as but not limited to targeting and/or navigation and/or facial expression recognition or object recognition task(s), can be recorded using an input device of the cognitive platform. Non-limiting examples of such input devices can include a touch, swipe or other gesture relative to a user interface or image capture device (such as but not limited to a touch-screen or other pressure sensitive screen, or a camera), including any form of graphical user interface configured for recording a user interaction. In other non-limiting examples, the user response recorded using the cognitive platform for tasks, such as but not limited to targeting and/or navigation and/or facial expression recognition or object recognition task(s), can include user actions that cause changes in a position, orientation, or movement of a computing device including the cognitive platform. Such changes in a position, orientation, or movement of a computing device can be recorded using an input device disposed in or otherwise coupled to the computing device, such as but not limited to a sensor. Non-limiting examples of sensors include a motion sensor, position sensor, ambient, gravity, gyroscope, light, magnetic, temperature, humidity, and/or an image capture device (such as but not limited to a camera).

In an example implementation involving multi-tasking tasks, the computer device is configured (such as using at least one specially-programmed processing unit) to cause the cognitive platform to present to a user two or more different type of tasks, such as but not limited to, targeting and/or navigation and/or facial expression recognition or object recognition tasks, or engagement tasks, during a short time frame (including in real-time and/or substantially simultaneously). The computer device is also configured (such as using at least one specially programmed processing unit) to collect data indicative of the type of user response received to the multi-tasking tasks, within the short time frame (including in real-time and/or substantially simultaneously). In these examples, the two or more different types of tasks can be presented to the individual within the short time frame (including in real-time and/or substantially simultaneously), and the computing device can be configured to receive data indicative of the user response(s) relative to the two or more different types of tasks within the short time frame (including in real-time and/or substantially simultaneously).

In some examples, the short time frame can be of any time interval at a resolution of up to about 1.0 millisecond or greater. The time intervals can be, but are not limited to, durations of time of any division of a periodicity of about 2.0 milliseconds or greater, up to any reasonable end time. The time intervals can be, but are not limited to, about 3.0 millisecond, about 5.0 millisecond, about 10 milliseconds, about 25 milliseconds, about 40 milliseconds, about 50 milliseconds, about 60 milliseconds, about 70 milliseconds, about 100 milliseconds, or greater. In other examples, the short time frame can be, but is not limited to, fractions of a second, about a second, between about 1.0 and about 2.0 seconds, or up to about 2.0 seconds, or more.

In some examples, the platform product or cognitive platform can be configured to collect data indicative of a reaction time of a user's response relative to the time of presentation of the tasks. For example, the computing device can be configured to cause the platform product or cognitive platform to provide smaller or larger reaction time window for a user to provide a response to the tasks as a way of adjusting the difficulty level.

In some examples, the platform product or cognitive platform can be configured to collect data indicative of a reaction time of a user's response relative to the time of presentation of the tasks. For example, the computing device can be configured to cause the platform product or cognitive platform to provide smaller or larger reaction time window for a user to provide a response to the tasks as a way of monitoring user engagement or adherence.

As used herein, the term "computerized stimuli or interaction" or "CSI" refers to a computerized element that is presented to a user to facilitate the user's interaction with a stimulus or other interaction. As non-limiting examples, the computing device can be configured to present auditory stimulus or initiate other auditory-based interaction with the user, and/or to present vibrational stimuli or initiate other vibrational-based interaction with the user, and/or to present tactile stimuli or initiate other tactile-based interaction with the user, and/or to present visual stimuli or initiate other visual-based interaction with the user.

Any task according to the principles herein can be presented to a user via a computing device, actuating component, or other device that is used to implement one or more stimuli or other interactive element. For example, the task can be presented to a user by rendering a graphical user interface to present the computerized stimuli or interaction (CSI) or other interactive elements. In other examples, the task can be presented to a user as auditory, tactile, or vibrational computerized elements (including CSIs) using an actuating component. Description of use of (and analysis of data from) one or more CSIs in the various examples herein also encompasses use of (and analysis of data from) tasks comprising the one or more CSIs in those examples.

In an example where the computing device is configured to present visual CSI, the CSI can be rendered using at least one graphical user interface to be presented to a user. In some examples, at least one graphical user interface is configured for measuring responses as the user interacts with CSI computerized element rendered using the at least one graphical user interface. In a non-limiting example, the graphical user interface can be configured such that the CSI computerized element(s) are active, and may require at least one response from a user, such that the graphical user interface is configured to measure data indicative of the type or degree of interaction of the user with the platform product. In another example, the graphical user interface can be configured such that the CSI computerized element(s) are a passive and are presented to the user using the at least one graphical user interface but may not require a response from the user. In this example, the at least one graphical user interface can be configured to exclude the recorded response of an interaction of the user, to apply a weighting factor to the data indicative of the response (e.g., to weight the response to lower or higher values), or to measure data indicative of the response of the user with the platform product as a measure of a misdirected response of the user (e.g., to issue a notification or other feedback to the user of the misdirected response). In this example, the at least one graphical user interface can be configured to exclude the recorded response of an interaction of the user, to apply a weighting factor to the data indicative of the response (e.g., to weight the response to lower or higher values), or to measure data indicative of the response of the user with the platform product as a measure of user engagement or adherence to one or more tasks.

In an example, the cognitive platform and/or platform product can be configured as a processor-implemented system, method or apparatus that includes and at least one processing unit. In an example, the at least one processing unit can be programmed to render at least one graphical user interface to present the computerized stimuli or interaction (CSI) or other interactive elements to the user for interaction. In other examples, the at least one processing unit can be programmed to cause an actuating component of the platform product to effect auditory, tactile, or vibrational computerized elements (including CSIs) to affect the stimulus or other interaction with the user. The at least one processing unit can be programmed to cause a component of the program product to receive data indicative of at least one user response based on the user interaction with the CSI or other interactive element (such as but not limited to cData), including responses provided using the input device. In an example where at least one graphical user interface is rendered to present the computerized stimuli or interaction (CSI) or other interactive elements to the user, the at least one processing unit can be programmed to cause graphical user interface to receive the data indicative of at least one user response. The at least one processing unit also can be programmed to: analyze the cData to provide a measure of the individual's cognitive condition, and/or analyze the differences in the individual's performance based on determining the differences between the user's responses (including based on differences in the cData), and/or adjust the difficulty level of the auditory, tactile, or vibrational computerized elements (including CSIs), the CSIs or other interactive elements based on the analysis of the cData (including the measures of the individual's performance determined in the analysis), and/or provide an output or other feedback from the platform product that can be indicative of the individual's performance, engagement, adherence to tasks, and/or cognitive assessment, and/or response to cognitive treatment, and/or assessed measures of cognition. In non-limiting examples, the at least one processing unit also can be programmed to classify an individual as to differences in cognition between individuals (including children) diagnosed with Attention Deficit Hyperactivity Disorder and autism spectrum disorders, and/or potential efficacy of use of the cognitive platform and/or platform product when the individual is administered a drug, biologic or other pharmaceutical agent, based on the cData collected from the individual's interaction with the cognitive platform and/or platform product and/or metrics computed based on the analysis (and associated computations) of that cData. In non-limiting examples, the at least one processing unit also can be programmed to classify an individual as to likelihood of onset and/or stage of progression of a neuropsychological condition, including as to a neurodegenerative condition, based on the cData collected from the individual's interaction with the cognitive platform and/or platform product and/or metrics computed based on the analysis (and associated computations) of that cData. The neurodegenerative condition can be, but is not limited to, Alzheimer's disease, dementia, Parkinson's disease, cerebral amyloid angiopathy, familial amyloid neuropathy, or Huntington's disease.

In other examples, the platform product can be configured as a processor-implemented system, method or apparatus that includes a display component, an input device, and the at least one processing unit. The at least one processing unit can be programmed to render at least one graphical user interface, for display at the display component, to present the computerized stimuli or interaction (CSI) or other interactive elements to the user for interaction. In other examples, the at least one processing unit can be programmed to cause an actuating component of the platform product to effect auditory, tactile, or vibrational computerized elements (including CSIs) to affect the stimulus or other interaction with the user.

Non-limiting examples of an input device include a touchscreen, or other pressure-sensitive or touch-sensitive surface, a motion sensor, a position sensor, a pressure sensor, joystick, exercise equipment, and/or an image capture device (such as but not limited to a camera).

In any example, the input device is configured to include at least one component configured to receive input data indicative of a physical action of the individual(s), where the data provides a measure of the physical action of the individual(s) in interacting with the cognitive platform and/or platform product, e.g., to perform the one or more tasks and/or tasks with interference.

The analysis of the individual's performance may include using the computing device to compute percent accuracy, number of hits and/or misses during a session or from a previously completed session. Other indicia that can be used to compute performance measures is the amount time the individual takes to respond after the presentation of a task (e.g., as a targeting stimulus). Other indicia can include, but are not limited to, reaction time, response variance, number of correct hits, omission errors, false alarms, learning rate, spatial deviance, subjective ratings, and/or performance threshold, etc.

In a non-limiting example, the user's performance can be further analyzed to compare the effects of two different types of tasks on the user's performances, where these tasks present different types of interferences (e.g., a distraction or an interrupter).

The computing device is configured to present the different types of interference as CSIs or other interactive elements that divert the user's attention from a primary task. For a distraction, the computing device is configured to instruct the individual to provide a primary response to the primary task and not to provide a response (i.e., to ignore the distraction). For an interrupter, the computing device is configured to instruct the individual to provide a response as a secondary task, and the computing device is configured to obtain data indicative of the user's secondary response to the interrupter within a short time frame (including at substantially the same time) as the user's response to the primary task (where the response is collected using at least one input device). The computing device is configured to compute measures of one or more of a user's performance at the primary task without an interference, performance with the interference being a distraction, and performance with the interference being an interruption. The user's performance metrics can be computed based on these measures. For example, the user's performance can be computed as a cost (performance change) for each type of interference (e.g., distraction cost and interrupter/multi-tasking cost). The user's performance level on the tasks can be analyzed and reported as feedback, including either as feedback to the cognitive platform for use to adjust the difficulty level of the tasks, and/or as feedback to the individual concerning the user's status or progression. In another example, the user's engagement or adherence level can be computed as a cost (performance change) for each type of interference (e.g., distraction cost and interruptor/multi-tasking cost). The user's engagement or adherence level on the tasks can be analyzed and reported as feedback, including either as feedback to the cognitive platform for use to monitor user's engagement or adherence, adjust types of tasks, and/or as feedback to the individual concerning the user's interaction with the computing device.

In a non-limiting example, the computing device can also be configured to analyze, store, and/or output the reaction time for the user's response and/or any statistical measures for the individual's performance (e.g., percentage of correct or incorrect response in the last number of sessions, over a specified duration of time, or specific for a type of tasks (including non-target and/or target stimuli, a specific type of task, etc.). In another non-limiting example, the computing device can also be configured to analyze, store, and/or output the reaction time for the user's response and/or any statistical measures for the individual's engagement or adherence level.

In a non-limiting example, the computing device can also be configured to apply a machine learning tool to the cData, including the records of data corresponding to stimuli presented to the user at the user interface and the responses of the user to the stimuli as reflected in measured sensor data (such as but not limited to accelerometer measurement data and/or touch screen measurement data), to characterize either something about the user (such as but not limited to an indication of a diagnosis and/or a measure of a severity of an impairment of the user) or the current state of the user (such as but not limited to an indication of degree to which the user is paying attention and giving effort to their interaction with the stimuli and related tasks presented by the cognitive platform and/or platform product). The quantifier of amount/degree of effort can indicate the user is giving little to no effort to the stimuli to perform the task(s) (e.g., paying little attention), or is giving a moderate amount of effort to the stimuli to perform the task(s) (e.g., paying a moderate amount of attention), or is giving best effort to the stimuli to perform the task(s) (e.g., paying great amount of attention). The quantifier of amount/degree of effort can also indicate the user's engagement or adherence to perform the task(s) (e.g., paying little attention), or is giving a moderate amount of effort to the stimuli to perform the task(s) (e.g., paying a moderate amount of attention), or is giving best effort to the stimuli to perform the task(s) (e.g., paying great amount of attention).

In any example herein, the computing device can be configured to apply machine learning tools that implement deep learning techniques including convolutional neural networks (CNNs) to derive patterns from the stimuli (and related tasks) presented by the cognitive platform and/or platform product to the user. In any example herein, the computing device can be configured to apply machine learning tools that implement deep learning techniques including either CNNs, or recurrent neural networks (RNNs), or a combination of CNNs and RNNs, to derive patterns from the sensor data indicative of the user responses to the stimuli and the temporal relationship of the sensor measurement of the user responses to the stimuli.

In any example herein, the computing device can be configured to train the machine learning tools implementing the deep learning techniques using training sets of data. The training set of data can include measurement data that is labeled manually based on users that are classified as to diagnosis or other classification, or other measurements (e.g., one or more measures of symptom severity, objective functioning and/or level of engagement) could be used to drive regression-based learning.

In any example herein, the computing device can be configured to characterize different user play sessions based on generation of an effort metric (which can be generated as the quantifiable measure of the amount/degree of effort). The example effort metric can be generated by applying the deep learning techniques described hereinabove to the cData and nData.

In any example herein, the computing device can be configured to apply the deep learning techniques to derive the effort metric to provide an overall measure of how much a given user is engaging effortfully with the stimuli and related tasks in a configuration where the cognitive platform is presenting a treatment.

In an example, based on the derived effort metric, the computing device can be further configured to provide feedback (such as but not limited to one or more messages, notifications, alarms, or other alerts) to the user that they are not putting in enough effort in to get the optimal results of the treatment.

In an example, the computing device can be further configured to detect an unengaged state, or a degree of engagement below a threshold, based on the generation of the effort metric at any one or more timepoints as the user is interacting with the one or more stimuli (and related tasks) presented by the cognitive platform. Based on the detection of the unengaged state, or the degree of engagement below a threshold, the computing device can be further configured to trigger feedback (such as but not limited to one or more messages, notifications, alarms, or other alerts) to the user so the user can adjust performance of the task(s) and provide responses to the stimuli such that the value of the effort metric (computed based on the measured cData and/or nData) indicates the user is back on track to get the optimal results of the treatment.

In a non-limiting example, the computerized element includes at least one task rendered at a graphical user interface as a visual task or presented as an auditory, tactile, or vibrational task. Each task can be rendered as interactive mechanics that are designed to elicit a response from a user after the user is exposed to stimuli for the purpose of cData and/or nData collection.

In a non-limiting example, the computerized element includes at least one platform interaction (gameplay) element of the platform rendered at a graphical user interface, or as auditory, tactile, or vibrational element of a program product. Each platform interaction (gameplay) element of the platform product can include interactive mechanics (including in the form of videogame-like mechanics) or visual (or cosmetic) features that may or may not be targets for cData and/or nData collection.

As used herein, the term "gameplay" encompasses a user interaction (including other user experience) with aspects of the platform product.

In a non-limiting example, the computerized element includes at least one element to indicate positive feedback to a user. Each element can include an auditory signal and/or a visual signal emitted to the user that indicates success at a task or other platform interaction element, i.e., that the user responses at the platform product has exceeded a threshold success measure on a task or platform interaction (gameplay) element.

In a non-limiting example, the computerized element includes at least one element to indicate negative feedback to a user. Each element can include an auditory signal and/or a visual signal emitted to the user that indicates failure at a task or platform interaction (gameplay) element, i.e., that the user responses at the platform product has not met a threshold success measure on a task or platform interaction element.

In a non-limiting example, the computerized element includes at least one element for messaging, i.e., a communication to the user that is different from positive feedback or negative feedback.

In a non-limiting example, the computerized element includes at least one element for indicating a reward. A reward computer element can be a computer-generated feature that is delivered to a user to promote user satisfaction with the CSIs and as a result, increase positive user interaction (and hence enjoyment of the user experience).

In a non-limiting example, the cognitive platform can be configured to render multi-task interactive elements. In some examples, the multi-task interactive elements are referred to as multi-task gameplay (MTG). The multi-task interactive elements include interactive mechanics configured to engage the user in multiple temporally overlapping tasks, i.e., tasks that may require multiple, substantially simultaneous responses from a user.

In a non-limiting example, the cognitive platform can be configured to render single-task interactive elements. In some examples, the single-task interactive elements are referred to as single-task gameplay (STG). The single-task interactive elements include interactive mechanics configured to engage the user in a single task in a given time interval.

According to the principles herein, the term "cognition" or "cognitive" refers to the mental action or process of acquiring knowledge and understanding through thought, experience, and the senses. This includes, but is not limited to, psychological concepts/domains such as, executive function, memory, perception, attention, emotion, motor control, and interference processing. An example computer-implemented device according to the principles herein can be configured to collect data indicative of user interaction with a platform product, and to compute metrics that quantify user performance. The quantifiers of user performance can be used to provide measures of cognition (for cognitive assessment) or to provide measures of status or progress of a cognitive treatment.

According to the principles herein, the term "treatment" or "treat" refers to any manipulation of CSI in a platform product (including in the form of an APP) that results in a measurable improvement of the abilities of a user, such as but not limited to improvements related to cognition, a user's mood, emotional state, and/or level of engagement or attention to the cognitive platform. The degree or level of improvement can be quantified based on user performance measures as describe herein. In an example, the term "treatment" may also refer to a therapy.

According to the principles herein, the term "session" refers to a discrete time period, with a clear start and finish, during which a user interacts with a platform product to receive assessment or treatment from the platform product (including in the form of an APP).

According to the principles herein, the term "assessment" refers to at least one session of user interaction with CSIs or other feature(s) or element(s) of a platform product. The data collected from one or more assessments performed by a user using a platform product (including in the form of an APP) can be used as to derive measures or other quantifiers of cognition, or other aspects of a user's abilities.

According to the principles herein, the term "cognitive load" refers to the amount of mental resources that a user may need to expend to complete a task. This term also can be used to refer to the challenge or difficulty level of a task or gameplay.

In an example, the platform product comprises a computing device that is configured to present to a user a cognitive platform based on interference processing. In an example system, method and apparatus that implements interference processing, at least one processing unit is programmed to render at least one first graphical user interface or cause an actuating component to generate an auditory, tactile, or vibrational signal, to present first CSIs as a first task that requires a first type of response from a user. The example system, method and apparatus is also configured to cause the at least one processing unit to render at least one second graphical user interface or cause the actuating component to generate an auditory, tactile, or vibrational signal, to present second CSIs as a first interference with the first task, requiring a second type of response from the user to the first task in the presence of the first interference. In a non-limiting example, the second type of response can include the first type of response to the first task and a secondary response to the first interference. In another non-limiting example, the second type of response may not include, and be quite different from, the first type of response. The at least one processing unit is also programmed to receive data indicative of the first type of response and the second type of response based on the user interaction with the platform product (such as but not limited to cData), such as but not limited to by rendering the at least one graphical user interface to receive the data. The platform product also can be configured to receive nData indicative of measurements made before, during, and/or after the user interacts with the cognitive platform (including nData from measurements of physiological or monitoring components and/or cognitive testing components). The at least one processing unit also can be programmed to: analyze the cData and/or nData to provide a measure of the individual's condition (including physiological and/or cognitive condition), and/or analyze the differences in the individual's performance based on determining the differences between the measures of the user's first type and second type of responses (including based on differences in the cData) and differences in the associated nData. The at least one processing unit also can be programmed to: adjust the difficulty level of the first task and/or the first interference based on the analysis of the cData and/or nData (including the measures of the individual's performance and/or condition (including physiological and/or cognitive condition) determined in the analysis), and/or provide an output or other feedback from the platform product that can be indicative of the individual's performance, and/or cognitive assessment, and/or response to cognitive treatment, and/or assessed measures of cognition. In non-limiting examples, the at least one processing unit also can be programmed to classify an individual as to differences in cognition between individuals (including children) diagnosed with Attention Deficit Hyperactivity Disorder and autism spectrum disorders, and/or potential efficacy of use of the cognitive platform and/or platform product when the individual is administered a drug, biologic or other pharmaceutical agent, based on nData and the cData collected from the individual's interaction with the cognitive platform and/or platform product and/or metrics computed based on the analysis (and associated computations) of that cData and the nData. In non-limiting examples, the at least one processing unit also can be programmed to classify an individual as to likelihood of onset and/or stage of progression of a neuropsychological condition, including as to a neurodegenerative condition, based on nData and the cData collected from the individual's interaction with the cognitive platform and/or platform product and/or metrics computed based on the analysis (and associated computations) of that cData and the nData. The neurodegenerative condition can be, but is not limited to, Alzheimer's disease, dementia, Parkinson's disease, cerebral amyloid angiopathy, familial amyloid neuropathy, or Huntington's disease.

In an example, the feedback from the differences in the individual's performance based on determining the differences between the measures of the user's first type and second type of responses and the nData can be used as an input in the cognitive platform that indicates real-time performance of the individual during one or more session(s). The data of the feedback can be used as an input to a computation component of the computing device to determine a degree of adjustment that the cognitive platform makes to a difficulty level of the first task and/or the first interference that the user interacts within the same ongoing session and/or within a subsequently-performed session.

As a non-limiting example, the cognitive platform based on interference processing can be a cognitive platform based on one or more platform products by Akili Interactive Labs, Inc. (Boston, MA).

In an example system, method and apparatus according to the principles herein that is based on interference processing, the graphical user interface is configured such that, as a component of the interference processing, one of the discriminating features of the targeting task that the user responds to is a feature in the platform that displays an emotion, a shape, a color, and/or a position that serves as an interference element in interference processing.

An example system, method, and apparatus according to the principles herein includes a cognitive platform and/or platform product (including using an APP) that is configured to set baseline metrics of CSI levels/attributes in APP session(s) based on measurements nData indicative of physiological condition and/or cognition condition (including indicators of neuropsychological disorders), to increase accuracy of assessment and efficiency of treatment. The CSIs may be used to calibrate a nData component to individual user dynamics of nData.

An example system, method, and apparatus according to the principles herein includes a cognitive platform and/or platform product (including using an APP) that is configured to use nData to detect states of attentiveness or inattentiveness to optimize delivery of CSIs related to treatment or assessment.

An example system, method, and apparatus according to the principles herein includes a cognitive platform and/or platform product (including using an APP) that is configured to use analysis of nData with CSI cData to detect and direct attention to specific CSIs related to treatment or assessment through subtle or overt manipulation of CSIs.

An example system, method, and apparatus according to the principles herein includes a cognitive platform and/or platform product (including using an APP) that is configured to use analysis of CSIs patterns of cData with nData within or across assessment or treatment sessions to generate user profiles (including profiles of ideal, optimal, or desired user responses) of cData and nData and manipulate CSIs across or within sessions to guide users to replicate these profiles.

An example system, method, and apparatus according to the principles herein includes a cognitive platform and/or platform product (including using an APP) that is configured to monitor nData for indicators of parameters related to user engagement and to optimize the cognitive load generated by the CSIs to align with time in an optimal engaged state to maximize neural plasticity and transfer of benefit resulting from treatment. As used herein, the term "neural plasticity" refers to targeted re-organization of the central nervous system.

An example system, method, and apparatus according to the principles herein includes a cognitive platform and/or platform product (including using an APP) that is configured to monitor nData indicative of anger and/or frustration to promote continued user interaction (also referred to as "play") with the cognitive platform by offering alternative CSIs or disengagement from CSIs.

An example system, method, and apparatus according to the principles herein includes a cognitive platform and/or platform product (including using an APP) that is configured to change CSI dynamics within or across assessment or treatment sessions to optimize nData related to cognition or other physiological or cognitive aspects of the user.

An example system, method, and apparatus according to the principles herein includes a cognitive platform and/or platform product (including using an APP) that is configured to adjust the CSIs or CSI cognitive load if nData signals of task automation are detected, or the physiological measurements that relate to task learning show signs of attenuation.

An example system, method, and apparatus according to the principles herein includes a cognitive platform and/or platform product (including using an APP) that is configured to combine signals from CSI cData with nData to optimize individualized treatment promoting improvement of indicators of cognitive abilities, and thereby, cognition.

An example system, method, and apparatus according to the principles herein includes a cognitive platform and/or platform product (including using an APP) that is configured to use a profile of nData to confirm/verify/authenticate a user's identity.

An example system, method, and apparatus according to the principles herein includes a cognitive platform and/or platform product (including using an APP) that is configured to use nData to detect positive emotional response to CSIs in order to catalog individual user preferences to customize CSIs to optimize enjoyment and promote continued engagement with assessment or treatment sessions.

An example system, method, and apparatus according to the principles herein includes a cognitive platform and/or platform product (including using an APP) that is configured to generate user profiles of cognitive improvement (such as but not limited to, user profiles associated with users classified or known to exhibit improved working memory, attention, processing speed, and/or perceptual detection/discrimination), and deliver a treatment that adapts CSIs to optimize the profile of a new user as confirmed by profiles from nData.

An example system, method, and apparatus according to the principles herein includes a cognitive platform and/or platform product (including using an APP) that is configured to provide to a user a selection of one or more profiles configured for cognitive improvement.

An example system, method, and apparatus according to the principles herein includes a cognitive platform and/or platform product (including using an APP) that is configured to monitor nData from auditory and visual physiological measurements to detect interference from external environmental sources that may interfere with the assessment or treatment being performed by a user using a cognitive platform or program product.

An example system, method, and apparatus according to the principles herein includes a cognitive platform and/or platform product (including using an APP) that is configured to use cData and/or nData (including metrics from analyzing the data) as a determinant or to make a decision as to whether a user (including a patient using a medical device) is likely to respond or not to respond to a treatment (such as but not limited to a cognitive treatment and/or a treatment using a biologic, a drug or other pharmaceutical agent). For example, the system, method, and apparatus can be configured to select whether a user (including a patient using a medical device) should receive treatment based on specific physiological or cognitive measurements that can be used as signatures that have been validated to predict efficacy in a given individual or certain individuals of the population (e.g., individual(s) classified to a given group based on differences in cognition between individuals (including children) diagnosed with Attention Deficit Hyperactivity Disorder and autism spectrum disorders). Such an example system, method, and apparatus configured to perform the analysis (and associated computation) described herein can be used as a biomarker to perform monitoring and/or screening. As a non-limiting example, the example system, method and apparatus configured to provide a provide a quantitative measure of the degree of efficacy of a cognitive treatment (including the degree of efficacy in conjunction with use of a biologic, a drug or other pharmaceutical agent) for a given individual or certain individuals of the population (e.g., individual(s) classified to a given group based on differences in cognition between individuals (including children) diagnosed with Attention Deficit Hyperactivity Disorder and autism spectrum disorders). In some examples, the individual or certain individuals of the population may be classified as having a certain neurodegenerative condition.

An example system, method, and apparatus according to the principles herein includes a cognitive platform and/or platform product (including using an APP) that is configured to use nData to monitor a user's ability to anticipate CSI(s) and manipulate CSIs patterns and/or rules to disrupt user anticipation of response to CSIs, to optimize treatment or assessment in use of a cognitive platform or program product.

Non-limiting examples of analysis (and associated computations) that can be performed based on various combinations of different types of nData and cData are described. The following example analyses and associated computations can be implemented using any example system, method and apparatus according to the principles herein.

The example cognitive platform and/or platform product is configured to implement a classifier model trained using clinical trial data set that includes an indication of the differences in cognition between individuals (including children) diagnosed with attention deficit hyperactivity disorder and autism spectrum disorders.

The non-limiting example classifier model can be trained to generate predictors of the differences in cognition between individuals (including children) diagnosed with attention deficit hyperactivity disorder and autism spectrum disorders, using training cData and corresponding nData, and based on metrics collected from at least one interaction of users with an example cognitive platform and/or platform product. The training nData can includes data indicative of the cognitive status and age of each user that corresponds to cData collected for a given user (such as but not limited to that user's score from at least one interaction with any example cognitive platform and/or platform product herein). In some examples, the nData can include data indicative of the gender of the user. For example, the cData can be collected based on a limited user interaction, e.g., on the order of a few minutes, with any example cognitive platform and/or platform product herein. The length of time of the limited user interaction can be, e.g., about 5 minutes, about 7 minutes, about 10 minutes, about 15 minutes, about 20 minutes, or about 30 minutes. The example cognitive platform and/or platform product can be configured to implement an assessment session (such as but not limited to an assessment implemented using an AKILI® platform product).

The non-limiting example classifier model according to the principles herein can be trained to generate predictors of the differences in cognition between individuals (including children) diagnosed with attention deficit hyperactivity disorder and autism spectrum disorders, using training cData and corresponding nData, and based on metrics collected from a plurality of interactions of users with an example cognitive platform and/or platform product. The training nData can includes data indicative of the differences in cognition between individuals (including children) diagnosed with attention deficit hyperactivity disorder and autism spectrum disorders.

In some examples, the nData can include data indicative of the gender of the user. The corresponding cData is collected for a given user (such as but not limited to that user's score from at least one interaction with any example cognitive platform and/or platform product herein). For example, the cData can be collected based on a plurality of interaction sessions of a user using a cognitive platform and/or platform product herein, e.g., two or more interaction sessions. The length of time of each interaction session can be, e.g., about 5 minutes, about 7 minutes, about 10 minutes, about 15 minutes, about 20 minutes, or about 30 minutes. The example cognitive platform and/or platform product can be configured to implement the plurality of assessment sessions (such as but not limited to an assessment implemented using an AKILI® platform product).

Example systems, methods, and apparatus according to the principles herein also provide a cognitive platform and/or platform product (including using an APP) that is configured to implement computerized tasks to produce cData. The example cognitive platform and/or platform product can be configured to use cData from a user interaction as inputs to a classifier model that determines the differences in cognition between individuals (including children) diagnosed with attention deficit hyperactivity disorder and autism spectrum disorders to a high degree of accuracy using a classifier model. The example cognitive platform and/or platform product can be configured to use cData from a user interaction as inputs to a classifier model that determines the user's likelihood of onset and/or stage of progression of a neuropsychological condition, including as to a neurodegenerative condition and/or an executive function disorder, such as but not limited to attention deficit hyperactivity disorder (ADHD), sensory-processing disorder (SPD), mild cognitive impairment (MCI), Alzheimer's disease, multiple-sclerosis, schizophrenia, depression, or anxiety.

The example cognitive platform and/or platform product (including using an APP) can be configured to collect performance data from a single assessment procedure that is configured to sequentially present a user with tasks that challenge cognitive control and executive function to varying degrees, and use the resulting cData representative of time ordered performance measures as the basis for the determination of differences in cognition between individuals (including children) diagnosed with Attention Deficit Hyperactivity Disorder and autism spectrum disorders, or the user's likelihood of onset and/or stage of progression of a neuropsychological condition, including as to a neurodegenerative condition and/or an executive function disorder, using a classifier model.

The example cognitive platforms or platform products are configured to present assessments that sufficiently challenge a user's cognitive control, attention, working memory, and task engagement.

The example classifier models according to the principles herein can be used to predict, with a greater degree of accuracy, differences in cognition between individuals (including children) diagnosed with Attention Deficit Hyperactivity Disorder and autism spectrum disorders, and/or the user's likelihood of onset and/or stage of progression of a neuropsychological condition, including as to a neurodegenerative condition and/or an executive function disorder, based on data (including cData) generated from a user's first interaction with the example cognitive platform and/or platform product (e.g., as an initial screening).

The example classifier models according to the principles herein can be used to predict, with a greater degree of accuracy, differences in cognition between individuals (including children) diagnosed with Attention Deficit Hyperactivity Disorder and autism spectrum disorders, and/or the user's likelihood of onset and/or stage of progression of a neuropsychological condition, including as to a neurodegenerative condition and/or an executive function disorder, based on a comparison of data (including cData) generated from a user's first moments of interaction with the example cognitive platform and/or platform product and the subsequent moments of interaction with the example cognitive platform and/or platform product.

In a non-limiting example, the example analyses (and associated computations) can be implemented by applying one or more linear mixed model regression models to the data (including data and metrics derived from the cData and/or nData). As a non-limiting example, the analysis can be based on a covariate adjustment of comparisons of data for given individuals, i.e., an analysis of factors with multiple measurements (usually longitudinal) for each individual. As a non-limiting example, the analysis can be caused to account for the correlation between measurements since the data originates from the same source. In this example as well, the analysis can be based on a covariate adjustment of comparisons of data between individuals using a single dependent variable or multiple variables.

In each example implementation, the cData is obtained based on interactions of each individual with any one or more of the example cognitive platforms and/or platform products described herein.

In a non-limiting example implementation, the cData used can be derived as described herein using an example cognitive platform and/or platform product that is configured to implement a sequence that could include at least one initial assessment session. Examples of additional assessments can include a first challenge session, a first training session, a second training session, and/or a second challenge session. The cData is collected based on measurements of the responses of the individual with the example cognitive platform and/or platform product during one or more segments of the assessment(s). For example, the cData can include data collected by the cognitive platform and/or platform product to quantify the interaction of the individual with the first moments of an initial assessment as well as data collected to quantify the interaction of the individual with the subsequent moments of an initial assessment. In another example, the cData can include data collected by the cognitive platform and/or platform product to quantify the interaction of the individual with the initial assessment as well as data collected to quantify the interaction of the individual with one or more additional assessments0 For one or more of the sessions (i.e., sessions of the initial assessments and/or the additional assessment), the example cognitive platform and/or platform product can be configured to present computerized tasks and platform interactions that inform cognitive assessment (screening or monitoring) or deliver treatment. The tasks can be single-tasking tasks and/or multi-tasking tasks (that include primary tasks with an interference). One or more of the tasks can include CSIs.

Non-limiting examples of the types of cData that can be derived from the interactions of an individual with the cognitive platform and/or platform product are as follows. The cData can be one or more scores generated by the cognitive platform and/or platform product based on the individual's response(s) in performance of a single-tasking task presented by the cognitive platform and/or platform product. The single-tasking task can be, but is not limited to, a targeting task, a navigation task, a facial expression recognition task, or an object recognition task. The cData can be one or more scores generated by the cognitive platform and/or platform product based on the individual's response(s) in performance of a multi-tasking task presented by the cognitive platform and/or platform product. The multi-tasking task can include a targeting task and/or a navigation task and/or a facial expression recognition task and/or an object recognition task, where one or more of the multi-tasking tasks can be presented as an interference with one or more primary tasks. The cData collected can be a scoring representative of the individual's response(s) to each task of the multi-task task(s) presented, and/or combination scores representative of the individual's overall response(s)

to the multi-task task(s). The combination score can be derived based on computation using any one or more of the scores collected from the individual's response(s) to each task of the multi-task task(s) presented, such as but not limited to a mean, mode, median, average, difference (or delta), standard deviation, or other type of combination. In a non-limiting example, the cData can include measures of the individual's reaction time to one or more of the tasks. The cData can be generated based on an analysis (and associated computation) performed using the other cData collected or derived using the cognitive platform and/or platform product. The analysis can include computation of an interference cost or other cost function. The cData can also include data indicative of an individual's compliance with a pre-specified set and type of interactions with the cognitive platform and/or platform product, such as but not limited to a percentage completion of the pre-specified set and type of interactions. The cData can also include data indicative of an individual's progression of performance using the cognitive platform and/or platform product, such as but not limited to a measure of the individual's score versus a pre-specified trend in progress.

In the non-limiting example implementations, the cData can be collected from a user interaction with the example cognitive platform and/or platform product at one or more specific timepoints: an initial timepoint (T1) representing an endpoint of the first moments (as defined herein) of an initial assessment session, and at a second timepoint (T2) and/or at a third timepoint (T3) representing endpoints of the subsequent moments of the initial assessment session.

In the non-limiting example implementations, the example cognitive platform and/or platform product can be configured for interaction with the individual over multiple different assessment sessions. In an example, the cData can be collected at timepoints Ti associated with the initial assessment session and later timepoints TL associated with the interactions of the individual with the multiple additional assessment sessions. For one or more of these multiple different sessions, the example cognitive platform and/or platform product can be configured for screening, for monitoring, and/or for treatment, as described in the various examples herein.

In a non-limiting example implementation, the example analyses (and associated computations) can be implemented based at least in part on the cData and nData such as but not limited to data indicative of age, gender, and fMRI measures (e.g., brain functional activity changes). The results of these example analyses (and associated computations) can be used to provide data indicative of differences in cognition between individuals (including children) diagnosed with Attention Deficit Hyperactivity Disorder and autism spectrum disorders, and/or the individual's likelihood of onset and/or stage of progression of a neuropsychological condition, including as to a neurodegenerative condition and/or an executive function disorder. As described herein, the example cData and nData can be used to train an example classifier model. The example classifier model can be implemented using a cognitive platform and/or platform product to provide data indicative of differences in cognition between individuals (including children) diagnosed with attention deficit hyperactivity disorder and autism spectrum disorders, and/or indicate the user's likelihood of onset and/or stage of progression of a neuropsychological condition, including as to a neurodegenerative condition and/or an executive function disorder.

A non-limiting example classifier model can be configured to perform the analysis (and associated computation)

using the cData and nData based on various analysis models. Differing analysis models can be applied to data collected from user interactions with the cognitive platform or the platform product (cData) collected at initial timepoints (T1 and/or or Ti) and at later timepoints (T2, and/or T3, and/or TL). The analysis model can be based on an ANCOVA model and/or a linear mixed model regression model, applied to a restricted data set (based on age and gender nData) or a larger data set (based on age, gender, fMRI, and other nData). The example cognitive platform or platform product can be used to collect cData at initial timepoints (T1 and/or or Ti) and at later timepoints (T2, and/or T3, and/or TL), to apply the classifier model to compare the cData collected at initial timepoints (T1 and/or or Ti) to the cData collected at later timepoints (T2, and/or T3, and/or TL) to derive an indicator of differences in cognition between individuals (including children) diagnosed with Attention Deficit Hyperactivity Disorder and autism spectrum disorders, and/or that indicates the user's likelihood of onset and/or stage of progression of a neuropsychological condition, including as to a neurodegenerative condition and/or an executive function disorder.

In a non-limiting example classifier model, the analysis (and associated computation) can be performed to determine a measure of the sensitivity and specificity of the cognitive platform or the platform product to identify and classify the individuals of the population as to differences in cognition between individuals (including children) diagnosed with Attention Deficit Hyperactivity Disorder and autism spectrum disorders, based on applying a logistic regression model to the data collected (including the cData and/or the nData).

The example analysis (and associated computation) can be performed by comparing each variable using any example model described herein for the nData corresponding to the drug group along with a covariate set. The example analysis (and associated computation) also can be performed by comparing effects of group classification (such as but not limited to grouping based on differences in cognition between individuals (including children) diagnosed with Attention Deficit Hyperactivity Disorder and autism spectrum disorders) versus drug interactions, where the cData (from performance of single-tasking tasks and/or multi-tasking tasks) are compared to determine the efficacy of the drug on the individual's performance. The example analysis (and associated computation) also can be performed by comparing effects of group classification (such as but not limited to grouping based on differences in cognition between individuals (including children) diagnosed with Attention Deficit Hyperactivity Disorder and autism spectrum disorders) versus drug interactions for sessions of user interaction with the cognitive platform and/or platform product, where the cData (from performance of single-tasking tasks and/or multi-tasking tasks) are compared to determine the efficacy of the drug on the individual's performance. The example analysis (and associated computation) also can be performed by comparing effects of group classification (such as but not limited to grouping based on differences in cognition between individuals (including children) diagnosed with Attention Deficit Hyperactivity Disorder and autism spectrum disorders) versus drug interactions for sessions (and types of tasks) of user interaction with the cognitive platform and/or platform product, where the cData (from performance of single-tasking tasks and/or multi-tasking tasks) are compared to determine the efficacy of the drug on the individual's performance.

In this example implementation of a classifier model, certain cData collected from the individual's interaction with the tasks (and associated CSIs) presented by the cognitive platform and/or platform product, and/or metrics computed using the cData based on the analysis (and associated computations) described, can co-vary or otherwise correlate with the nData, such as but not limited to differences in cognition between individuals (including children) diagnosed with Attention Deficit Hyperactivity Disorder and autism spectrum disorders, and/or potential efficacy of use of the cognitive platform and/or platform product when the individual is administered a drug, biologic or other pharmaceutical agent. An example cognitive platform and/or platform product according to the principles herein can be configured to classify an individual as to differences in cognition between individuals (including children) diagnosed with Attention Deficit Hyperactivity Disorder and autism spectrum disorders, and/or potential efficacy of use of the cognitive platform and/or platform product when the individual is administered a drug, biologic or other pharmaceutical agent based on the cData collected from the individual's interaction with the cognitive platform and/or platform product and/or metrics computed based on the analysis (and associated computations). The example cognitive platform and/or platform product can include, or communicate with, a machine learning tool or other computational platform that can be trained using the cData and nData to perform the classification using the example classifier model.

An example cognitive platform and/or platform product configured to implement the classifier model provides certain attributes. The example cognitive platform and/or platform product can be configured to classify a user according to the differences in cognition between individuals (including children) diagnosed with attention deficit hyperactivity disorder and autism spectrum disorders, and/or the user's likelihood of onset and/or stage of progression of a neuropsychological condition, including as to a neurodegenerative condition and/or an executive function disorder, based on faster data collection. For example, the data collection from an assessment performed using the example cognitive platform and/or platform product herein can be in a few minutes (e.g., in as few as about 5 or 7 minutes for an example classifier model based on an initial screen). This is much faster than existing assessments, which can require lengthy office visits or time-consuming medical procedures. In an example where a classifier model based on multiple assessment sessions is implemented for additional accuracy, the time requirements are still acceptably short (e.g., up to about 40 minutes for a total of four (4) assessments).

An example cognitive platform and/or platform product herein configured to implement the classifier model can be easily and remotely deployable on a mobile device such as but not limited to a smart phone or tablet. Existing assessments may require clinician participation, may require the test to be performed in a laboratory/clinical setting, and/or may require invasive on-site medical procedures.

An example cognitive platform and/or platform product herein configured to implement the classifier model can be delivered in an engaging format (such as but not limited to a "game-like" format) that encourages user engagement and improves effective use of the assessment, thus increases accuracy.

An example cognitive platform and/or platform product herein configured to implement the classifier model can be configured to combine orthogonal metrics from different tasks collected in a single session for highly accurate results.

An example cognitive platform and/or platform product herein configured to implement the classifier model provides an easily deployable, cost effective, engaging, short-duration assessment of differences in cognition between individuals (including children) diagnosed with Attention Deficit Hyperactivity Disorder and autism spectrum disorders, and/or indicate the user's likelihood of onset and/or stage of progression of a neuropsychological condition, including as to a neurodegenerative condition and/or an executive function disorder, with a high degree of accuracy.

As non-limiting examples, at least a portion of the example classifier model herein can be implemented in the source code of an example cognitive platform and/or platform product, and/or within a data processing application program interface housed in an internet server.

An example cognitive platform and/or platform product herein configured to implement the classifier model can be used to provide data indicative of differences in cognition between individuals (including children) diagnosed with attention deficit hyperactivity disorder and autism spectrum disorders to one or more of an individual, a physician, a clinician, or other medical or healthcare practitioner, or physical therapist.

An example cognitive platform and/or platform product herein configured to implement the classifier model can be used as a screening tool to determine differences in cognition between individuals (including children) diagnosed with Attention Deficit Hyperactivity Disorder and autism spectrum disorders, such as but not limited to, for clinical trials, or other drug trials, or for use by a private physician/clinician practice, and/or for an individual's self-assessment (with corroboration by a medical practitioner).

An example cognitive platform and/or platform product herein configured to implement the classifier model can be used as a screening tool to provide an accurate assessment of differences in cognition between individuals (including children) diagnosed with attention deficit hyperactivity disorder and autism spectrum disorders to inform if additional tests are to be performed to confirm or clarify status.

An example cognitive platform and/or platform product herein configured to implement the classifier model can be used in a clinical or private healthcare setting to provide an indication of differences in cognition between individuals (including children) diagnosed with attention deficit hyperactivity disorder and autism spectrum disorders without need for expensive traditional tests (which may be unnecessary).

As described hereinabove, the example systems, methods, and apparatus according to the principles herein can be implemented, using at least one processing unit of a programmed computing device, to provide the cognitive platform and/or platform product. FIG. 1 shows an example apparatus 500 according to the principles herein that can be used to implement the cognitive platform and/or platform product including the classifier model described hereinabove herein. The example apparatus 500 includes at least one memory 502 and at least one processing unit 504. The at least one processing unit 504 is communicatively coupled to the at least one memory 502.

Example memory 502 can include, but is not limited to, hardware memory, non-transitory tangible media, magnetic storage disks, optical disks, flash drives, computational device memory, random access memory, such as but not limited to DRAM, SRAM, EDO RAM, any other type of memory, or combinations thereof. Example processing unit 504 can include, but is not limited to, a microchip, a processor, a microprocessor, a special purpose processor, an application specific integrated circuit, a microcontroller, a field programmable gate array, any other suitable processor, or combinations thereof.

The at least one memory 502 is configured to store processor-executable instructions 506 and a computing component 508. In a non-limiting example, the computing component 508 can be used to analyze the cData and/or nData received from the cognitive platform and/or platform product coupled with the one or more physiological or monitoring components and/or cognitive testing components as described herein. As shown in FIG. 1, the memory 502 also can be used to store data 510, such as but not limited to the nData 512 (including computation results from application of an example classifier model, measurement data from measurement(s) using one or more physiological or monitoring components and/or cognitive testing components) and/or data indicative of the response of an individual to the one or more tasks (cData), including responses to tasks rendered at a graphical user interface of the apparatus 500 and/or tasks generated using an auditory, tactile, or vibrational signal from an actuating component coupled to or integral with the apparatus 500. The data 510 can be received from one or more physiological or monitoring components and/or cognitive testing components that are coupled to or integral with the apparatus 500.

In a non-limiting example, the at least one processing unit 504 executes the processor-executable instructions 506 stored in the memory 502 at least to analyze the cData and/or nData received from the cognitive platform and/or platform product coupled with the one or more physiological or monitoring components and/or cognitive testing components as described herein, using the computing component 508. The at least one processing unit 504 also can be configured to execute processor-executable instructions 506 stored in the memory 502 to apply the example classifier model to the cDdata and nData, to generate computation results indicative of the classification of an individual according to differences in cognition between individuals (including children) diagnosed with Attention Deficit Hyperactivity Disorder and autism spectrum disorders, and/or likelihood of onset and/or stage of progression of a neuropsychological condition, including as to a neurodegenerative condition and/or an executive function disorder. The at least one processing unit 504 also executes processor-executable instructions 506 to control a transmission unit to transmit values indicative of the analysis of the cData and/or nData received from the cognitive platform and/or platform product coupled with the one or more physiological or monitoring components and/or cognitive testing components as described herein, and/or controls the memory 502 to store values indicative of the analysis of the cData and/or nData.

In another non-limiting example, the at least one processing unit 504 executes the processor-executable instructions 506 stored in the memory 502 at least to apply signal detection metrics in computer-implemented adaptive response-deadline procedures.

Figure 2:
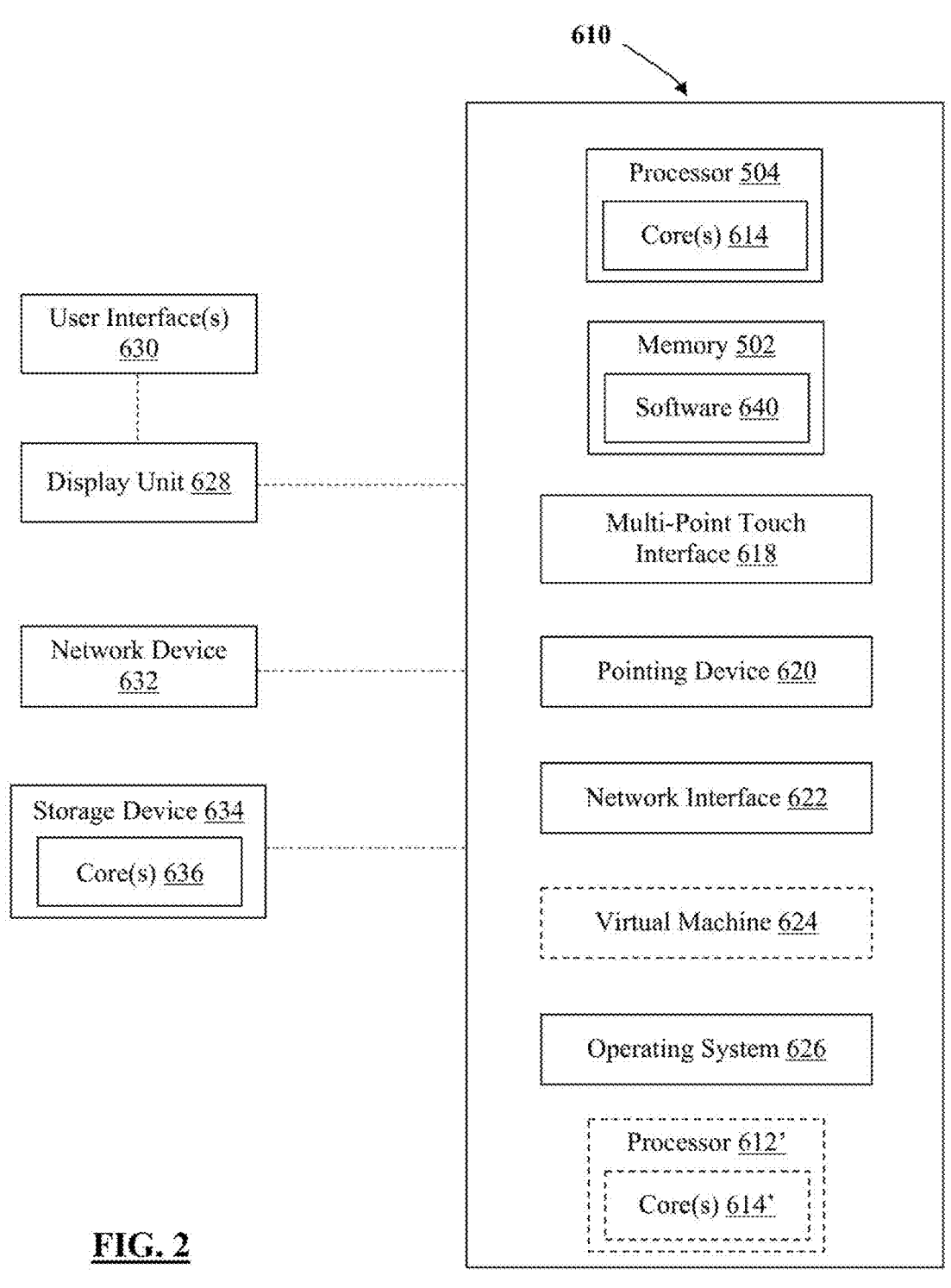
FIG. 2 is a functional block diagram of system architecture through which one or more aspects of the present disclosure may be implemented.

FIG. 2 is a block diagram of an example computing device 610 that can be used as a computing component according to the principles herein. In any example herein, computing device 610 can be configured as a console that receives user input to implement the computing component, including to apply the signal detection metrics in computer-implemented adaptive response-deadline procedures. For clarity, FIG. 2 also refers back to and provides greater detail regarding various elements of the example system of FIG. 1. The computing device 610 can include one or more non-transitory computer-readable media for storing one or more computer-executable instructions or software for implementing examples. The non-transitory computer-readable media can include, but are not limited to, one or more types of hardware memory, non-transitory tangible media (for example, one or more magnetic storage disks, one or more optical disks, one or more flash drives), and the like. For example, memory 502 included in the computing device 610 can store computer-readable and computer-executable instructions or software for performing the operations disclosed herein. For example, the memory 502 can store a software application 640 which is configured to perform various combinations of the disclosed operations (e.g., analyze cognitive platform and/or platform product measurement data and response data, apply an example classifier model, or performing a computation). The computing device 610 also includes configurable and/or programmable processor 504 and an associated core 614, and optionally, one or more additional configurable and/or programmable processing devices, e.g., processor(s) 612' and associated core (s) 614' (for example, in the case of computational devices having multiple processors/cores), for executing computer-readable and computer-executable instructions or software stored in the memory 502 and other programs for controlling system hardware. Processor 504 and processor(s) 612' can each be a single core processor or multiple core (614 and 614') processor.

Virtualization can be employed in the computing device 610 so that infrastructure and resources in the console can be shared dynamically. A virtual machine 624 can be provided to handle a process running on multiple processors so that the process appears to be using only one computing resource rather than multiple computing resources. Multiple virtual machines can also be used with one processor.

Memory 502 can include a computational device memory or random-access memory, such as but not limited to DRAM, SRAM, EDO RAM, and the like. Memory 502 can include a non-volatile memory, such as but not limited to a hard-disk or flash memory. Memory 502 can include other types of memory as well, or combinations thereof.

In a non-limiting example, the memory 502 and at least one processing unit 504 can be components of a peripheral device, such as but not limited to a dongle (including an adapter) or other peripheral hardware. The example peripheral device can be programmed to communicate with or otherwise coupled to a primary computing device, to provide the functionality of any of the example cognitive platform and/or platform product, apply an example classifier model, and implement any of the example analyses (including the associated computations) described herein. In some examples, the peripheral device can be programmed to directly communicate with or otherwise couple to the primary computing device (such as but not limited to via a USB or HDMI input), or indirectly via a cable (including a coaxial cable), copper wire (including, but not limited to, PSTN, ISDN, and DSL), optical fiber, or other connector or adapter. In another example, the peripheral device can be programmed to communicate wirelessly (such as but not limited to Wi-Fi or Bluetooth®) with primary computing device. The example primary computing device can be a smartphone (such as but not limited to an iPhone®, a BlackBerry®, or an Android™-based smartphone), a television, a workstation, a desktop computer, a laptop, a tablet, a slate, an electronic-reader (e-reader), a digital assistant, or other electronic reader or hand-held, portable, or wearable computing device, or any other equivalent device, an Xbox®, a Wii®, or other equivalent form of computing device.

A user can interact with the computing device 610 through a visual display unit 628, such as a computer monitor, which can display one or more user interfaces 630 that can be provided in accordance with example systems and methods. The computing device 610 can include other I/O devices for receiving input from a user, for example, a keyboard or any suitable multi-point touch interface 618, a pointing device 620 (e.g., a mouse), a camera or other image recording device, a microphone or other sound recording device, an accelerometer, a gyroscope, a sensor for tactile, vibrational, or auditory signal, and/or at least one actuator. The keyboard 618 and the pointing device 620 can be coupled to the visual display unit 628. The computing device 610 can include other suitable conventional I/O peripherals.

The computing device 610 can also include one or more storage devices 634 (including a single core processor or multiple core processor 636), such as a hard-drive, CD-ROM, or other computer readable media, for storing data and computer-readable instructions and/or software that perform operations disclosed herein. Example storage device 634 (including a single core processor or multiple core processor 636) can also store one or more databases for storing any suitable information required to implement example systems and methods. The databases can be updated manually or automatically at any suitable time to add, delete, and/or update one or more items in the databases.

The computing device 610 can include a network interface 622 configured to interface via one or more network devices 632 with one or more networks, for example, Local Area Network (LAN), metropolitan area network (MAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 622 can include a built-in network adapter, network interface card, PCMCIA network card, card bus network adapter, wireless network adapter, USB network adapter, modem or any other device suitable for interfacing the computing device 610 to any type of network capable of communication and performing the operations described herein. Moreover, the computing device 610 can be any computational device, such as a smartphone (such as but not limited to an iPhone®, a BlackBerry®, or an Android™-based smartphone), a television, a workstation, a desktop computer, a server, a laptop, a tablet, a slate, an electronic-reader (e-reader), a digital assistant, or other electronic reader or hand-held, portable, or wearable computing device, or any other equivalent device, an Xbox®, a Wii®, or other equivalent form of computing or telecommunications device that is capable of communication and that has or can be coupled to sufficient processor power and memory capacity to perform the operations described herein. The one or more network devices 632 may communicate using different types of protocols, such as but not limited to WAP (Wireless Application Protocol), TCP/IP (Transmission Control Protocol/Internet Protocol), NetBEUI (NetBIOS Extended User Interface), or IPX/SPX (Internetwork Packet Exchange/Sequenced Packet Exchange).

The computing device 610 can run any operating system 626, such as any of the versions of the Microsoft® Windows® operating systems, iOS® operating system, Android™ operating system, the different releases of the Unix and Linux operating systems, any version of the MacOS® for Macintosh computers, any embedded operating system, any real-time operating system, any open source operating system, any proprietary operating system, or any other operating system capable of running on the console and performing the operations described herein. In some examples, the operating system 626 can be run in native mode or emulated mode. In an example, the operating system 626 can be run on one or more cloud machine instances.

Any classification of an individual as to likelihood of onset and/or stage of progression of a neurodegenerative condition can be transmitted as a signal to a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in dosage of a drug, biologic or other pharmaceutical agent to the individual or to determine an optimal type or combination of drug, biologic or other pharmaceutical agent to the individual.

In some examples, the results of the analysis may be used to modify the difficulty level or other property of the computerized stimuli or interaction (CSI) or other interactive elements.

Figure 3A:
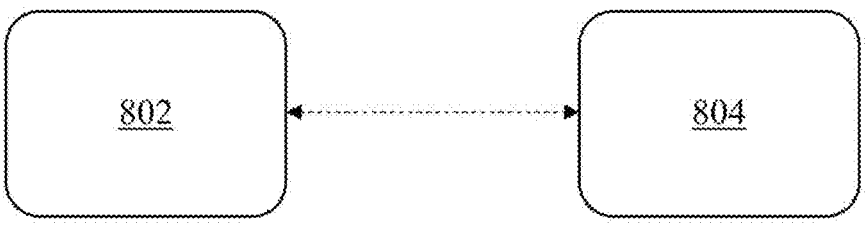
FIG. 3A is a system diagram of the cognitive platform of the present disclosure, in accordance with an embodiment.

FIG. 3A shows a non-limiting example system, method, and apparatus according to the principles herein, where the platform product (including using an APP) is configured as a cognitive platform 802 that is separate from, but configured for coupling with, one or more of the physiological components 804.

Figure 3B:
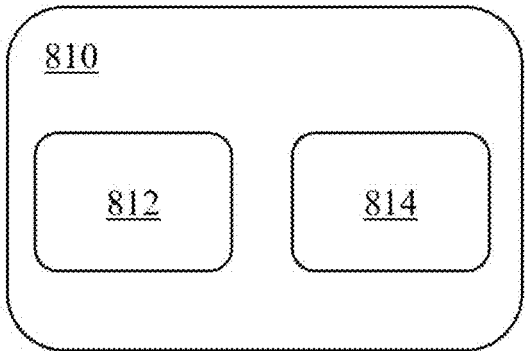
FIG. 3B is a system diagram of the cognitive platform of the present disclosure, in accordance with an embodiment.

FIG. 3B shows another non-limiting example system, method, and apparatus according to the principles herein, where the platform product (including using an APP) is configured as an integrated device 810, where the cognitive platform 812 that is integrated with one or more of the physiological components 814.

Figure 4:
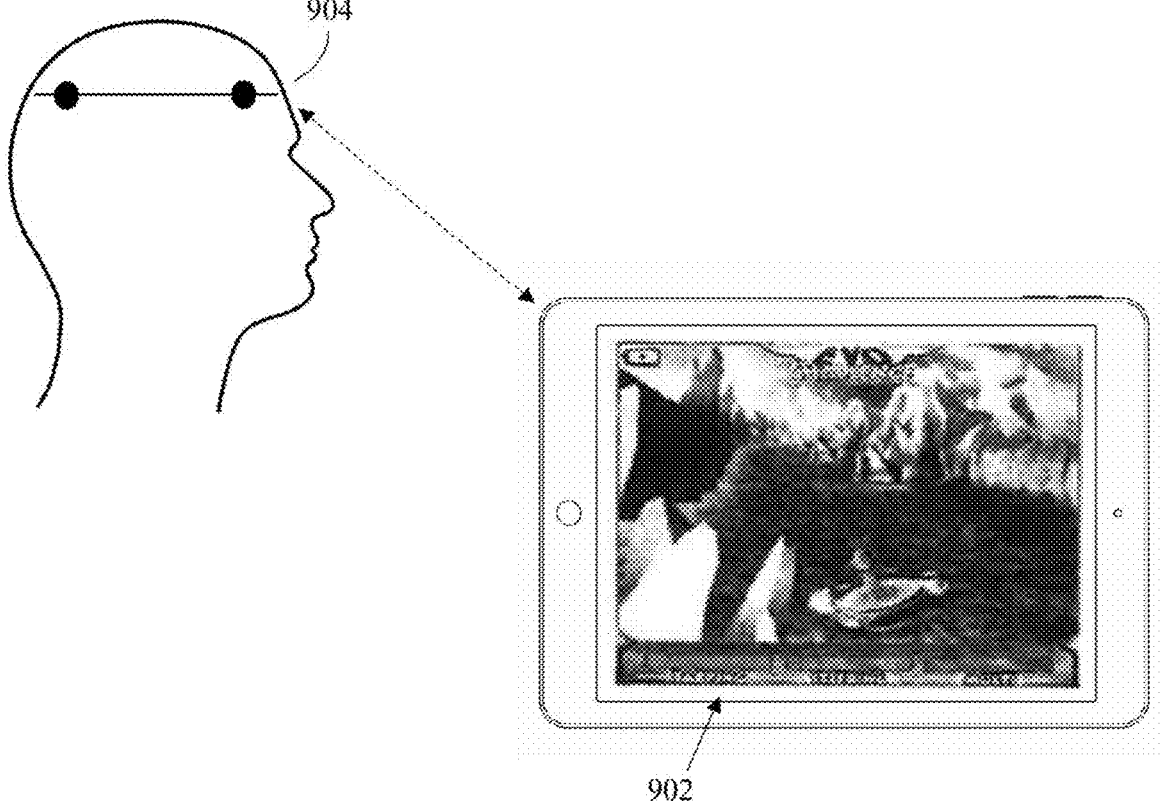
FIG. 4 is a system diagram of the cognitive platform of the present disclosure, in accordance with an embodiment.

FIG. 4 shows a non-limiting example implementation where the platform product (including using an APP) is configured as a cognitive platform 902 that is configured for coupling with a physiological component 904. In this example, the cognitive platform 902 is configured as a tablet including at least one processor programmed to implement the processor-executable instructions associated with the tasks and CSIs described hereinabove, to receive cData associated with user responses from the user interaction with the cognitive platform 902, to receive the nData from the physiological component 904, to analyze the cData and/or nData as described hereinabove, and to analyze the cData and/or nData to provide a measure of the individual's physiological condition and/or cognitive condition, and/or analyze the differences in the individual's performance based on determining the differences between the user's responses and the nData, and/or adjust the difficulty level of the computerized stimuli or interaction (CSI) or other interactive elements based on the individual's performance determined in the analysis and based on the analysis of the cData and/or nData, and/or provide an output or other feedback from the platform product indicative of the individual's performance, and/or cognitive assessment, and/or response to cognitive treatment, and/or assessed measures of cognition. In this example, the physiological component 904 is configured as an EEG mounted to a user's head, to perform the measurements before, during and/or after user interaction with the cognitive platform 902, to provide the nData.

Figure 5:
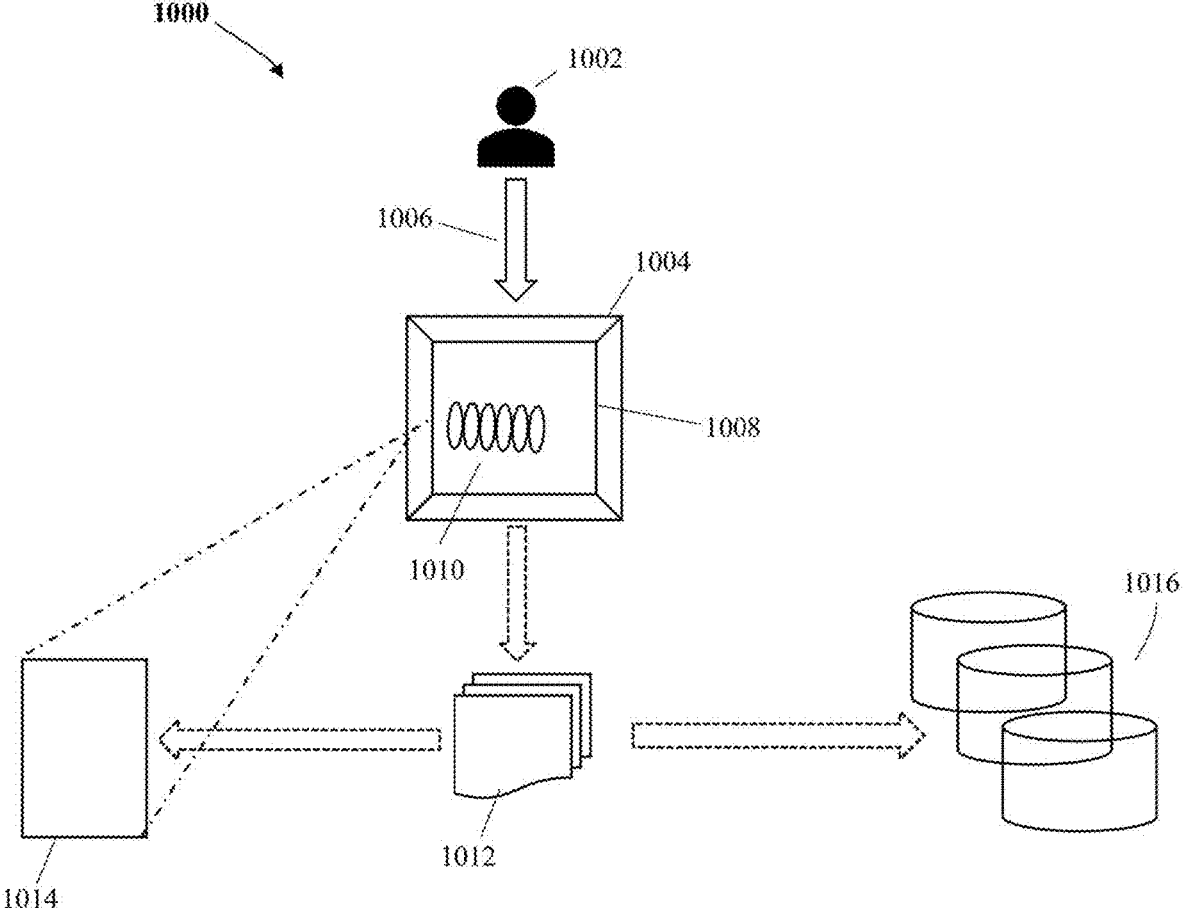
FIG. 5 is a schematic diagram of an aspect of the cognitive platform of the present disclosure, in accordance with an embodiment.

FIG. 5 is a schematic diagram of a routine 1000 of a cognitive platform for deriving an effort metric for optimizing a computer-assisted therapeutic treatment. In accordance with an embodiment, routine 1000 comprises presenting a user 1002 a mobile electronic device 1004 configured to receive a user input 1006 from a graphical user interface 1008 and rendering a graphical element/output 1010. In various implementations, graphical element/output 1010 comprises one or more computerized stimuli or interaction corresponding to one or more tasks or user prompts in a computerized therapeutic treatment regimen, diagnostic or predictive tool. The said stimuli or interaction generates a plurality of user generated data 1012 corresponding to the one or more tasks or user prompts. In one implementation, user generated data 1012 may be processed by computing unit 1014 which is integral within graphical user interface 1008. In an alternative implementation, user generated data 1012 may be transmitted and processed remotely on a remote computing server 1016. In various implementations, the said computing unit or computing server executes one or more instructions stored on a non-transitory computer readable medium to perform one or more actions. The actions include but are not limited to computing, computing tasks, modifying one or more interface elements rendered on graphical interface 1008, computing a measure of change in an effort metric. In one implementation, computing unit 1014 or server 1016 receives a plurality of user-generated data corresponding to the one or more tasks or user prompts. In another implementation, computing unit 1014 or server 1016 processes the plurality of user-generated data 1012 according to a non-linear computational model to derive an effort metric associated with the computerized therapeutic treatment regimen, diagnostic or predictive tool. In accordance with certain embodiments, the non-linear computational model comprises a convolutional neural network or a recurrent neural network. In another implementation, computing unit 1014 or server 1016 executes instructions to modify one or more interface elements rendered by graphical user interface 1008 in response to the effort metric. In another implementation, computing unit 1014 or server 1016 executes instructions to calculate a measure of change in the effort metric in response to modifying the one or more element/output 1010 rendered by the graphical user interface 1008. One or more embodiments of routine 1000 may be executed by computing unit 1014 or server 1016 in one or more non-limiting sequential, parallel, combination, permutation, or concurrent, or recursive manner.

The analysis of user 1002's performance or indicative of engagement or level of effort may include using the computing device 1004 to compute percent accuracy, number of hits and/or misses during a session or from a previously completed session. Other indicia that can be used to compute performance measures is the amount time the individual takes to respond after the presentation of a task (e.g., as a targeting stimulus). Other indicia can include, but are not limited to, reaction time, response variance, number of correct hits, omission errors, false alarms, learning rate, spatial deviance, subjective ratings, and/or performance threshold, etc. In a non-limiting example, the user's performance or indicative of engagement or level of effort or indicative of engagement can be further analyzed to compare the effects of two different types of tasks on the user's performances, where these tasks present different types of interferences (e.g., a distraction or an interrupter). In a non-limiting example, the user's performance can be further analyzed to compare the effects of two different types of tasks on the user's performances, where these tasks present different types of interferences (e.g., a distraction or an interrupter). For a distraction, the computing device 1004 is configured to instruct user 1002 to provide a primary response to the primary task and not to provide a response (i.e., to ignore the distraction). For an interrupter, the computing device is configured to instruct user 1002 to provide a response as a secondary task, and the computing device 1004 is configured to obtain data indicative of the user's secondary response to the interrupter within a short time frame (including at substantially the same time) as the user's response to the primary task (where the response is collected using at least one input device). The computing device 1004 is configured to compute measures of one or more of a user's performance, engagement, or level of effort at the primary task without an interference, performance, engagement, or level of effort with the interference being a distraction, and, performance, engagement, or level of effort with the interference being an interruption. The user's performance, engagement, or level of effort metrics can be computed based on these measures. For example, the user's performance, performance, engagement, or level of effort can be computed as a cost (performance change) for each type of interference (e.g., distraction cost and interrupter/multi-tasking cost). The user's performance, engagement, or level of effort level on the tasks can be analyzed and reported as feedback, including either as feedback to the cognitive platform for use to adjust the difficulty level of the tasks, and/or as feedback to the individual concerning the user's status or progression, performance, engagement, or level of effort. In another example, the user's engagement or adherence level on the tasks can be analyzed and reported as feedback, including either as feedback to the cognitive platform for use to monitor user's engagement or adherence, adjust types of tasks, and/or as feedback to the individual concerning the user's interaction with the computing device 1004.

In a non-limiting example, the computing device 1004 can also be configured to analyze, store, and/or output the reaction time for the user's response and/or any statistical measures for the individual's performance (e.g., percentage of correct or incorrect response in the last number of sessions, over a specified duration of time, or specific for a type of tasks (including non-target and/or target stimuli, a specific type of task, etc.). In another non-limiting example, the computing device 1004 can also be configured to analyze, store, and/or output the reaction time for the user's response and/or any statistical measures for the individual's engagement or adherence level.

In a non-limiting example, the computing device 1004 can also be configured to apply a machine learning tool to the cData, including the records of data corresponding to stimuli 1010 presented to the user at the graphical user interface 1008 and the responses of the user 1002 to the stimuli 1010 as reflected in measured sensor data (such as but not limited to accelerometer measurement data and/or touch screen measurement data), to characterize either something about the user 1002 (such as but not limited to an indication of a diagnosis and/or a measure of a severity of an impairment of the user) or the current state of the user (such as but not limited to an indication of degree to which the user is paying attention and giving effort to their interaction with the stimuli and related tasks. The quantifier of amount/degree of effort can indicate the user is giving little to no effort to the stimuli to perform the task(s) (e.g., paying little attention), or is giving a moderate amount of effort to the stimuli to perform the task(s) (e.g., paying a moderate amount of attention), or is giving best effort to the stimuli to perform the task(s) (e.g., paying great amount of attention). The quantifier of amount/degree of effort can also indicate the user's engagement or adherence to perform the task(s) (e.g., paying little attention), or is giving a moderate amount of effort to the stimuli to perform the task(s) (e.g., paying a moderate amount of attention), or is giving best effort to the stimuli to perform the task(s) (e.g., paying great amount of attention).

FIG. 6 is a schematic diagram of a routine 1100 for modifying one or more user interface elements of a cognitive platform of the present disclosure. In various implementations, mobile electronic device 1102, equivalent to mobile electronic device 1004 (as shown in FIG. 5), comprises a user interface 1104 capable of rending one or more graphical element/output/stimuli 1106*a*. The graphical element/output/stimuli 1106*a* comprises at least one user interface element, user prompt, notification, message, visual element of varying shape, color, color scheme, sizes, rate, frequency of rendering of a graphical output, visual stimuli, computerized stimuli, or the like. In one embodiment, the graphical element/output/stimuli 1106*a* is rendered, displayed, or presented in one state. In an alternative embodiment, the graphical element/output/stimuli 1106*a* is rendered, displayed, or presented in an altered state as graphical element/output/stimuli 1106*b* comprising at least one user interface element, user prompt, notification, message, visual element of varying shape, color, sizes, rendering of a graphical output, visual stimuli, computerized stimuli, or the like. In various implementations, the transition state or instance of graphical element/output/stimuli 1106*a* to graphical element/output/stimuli 1106*b* is dependent on a plurality of user data, user training data, input response to one or more computerized stimuli or interaction associated with a computerized therapeutic treatment regimen, diagnostic or predictive tool. In various embodiments, one or more state or instances is dependent on a determined or derived effort metric(s) or a determined measure of user engagement, a measure of change, adherence to instruction, or adherence to therapy. In various embodiments, the transition state or instance of graphical element/output/stimuli 1106*a* to graphical element/output/stimuli 1106*b* is dependent on one or more response to the measure of user engagement being below a specified threshold value.

In one illustrative example, the computing device 1102 can be configured to present auditory stimulus or initiate other auditory-based interaction with the user, and/or to present vibrational stimuli or initiate other vibrational-based interaction with the user, and/or to present tactile stimuli or initiate other tactile-based interaction with the user, and/or to present visual stimuli or initiate other visual-based interaction with the user. Any task according to the principles herein can be presented to a user via a computing device 1102, actuating component, or other device that is used to implement one or more stimuli 1106*a* and or changes of stimuli 1106*a* to alternate stimuli 1106*b*. For example, the task can be presented to a user by on rendering graphical user interface 1104 to present the computerized stimuli 1106*a* or interaction (CSI) or other interactive elements. In other examples, the task can be presented to a user as auditory, tactile, or vibrational computerized elements (including CSIs) using an actuating component. In an example where the computing device 1102 is configured to present visual CSI, the CSI can be rendered as a graphical element/output/stimuli 1106*a*, configured for measuring responses as the user interacts with the CSI computerized element in an active manner and requires at least one response from a user, to measure data indicative of the type or degree of interaction of the user, and to change the state of 1106a into 1106b to elicit a differing response. In another example, graphical element/output/stimuli 1106a is passive but may not require a response from the user. In this example, the graphical element/output/stimuli 1106a can be configured to exclude the recorded response of an interaction of the user, to apply a weighting factor to the data indicative of the response (e.g., to weight the response to lower or higher values), or to measure data indicative of the response of the user as a measure of a misdirected response of the user (e.g., to issue a notification or other feedback to the user of the misdirected response). In this example, the graphical element/output/ stimuli can be configured to exclude the recorded response of an interaction of the user, to apply a weighting factor to the data indicative of the response (e.g., to weight the response to lower or higher values), or to measure data indicative of the response of the user as a measure of user performance, engagement, or adherence to one or more tasks.

Figure 7:
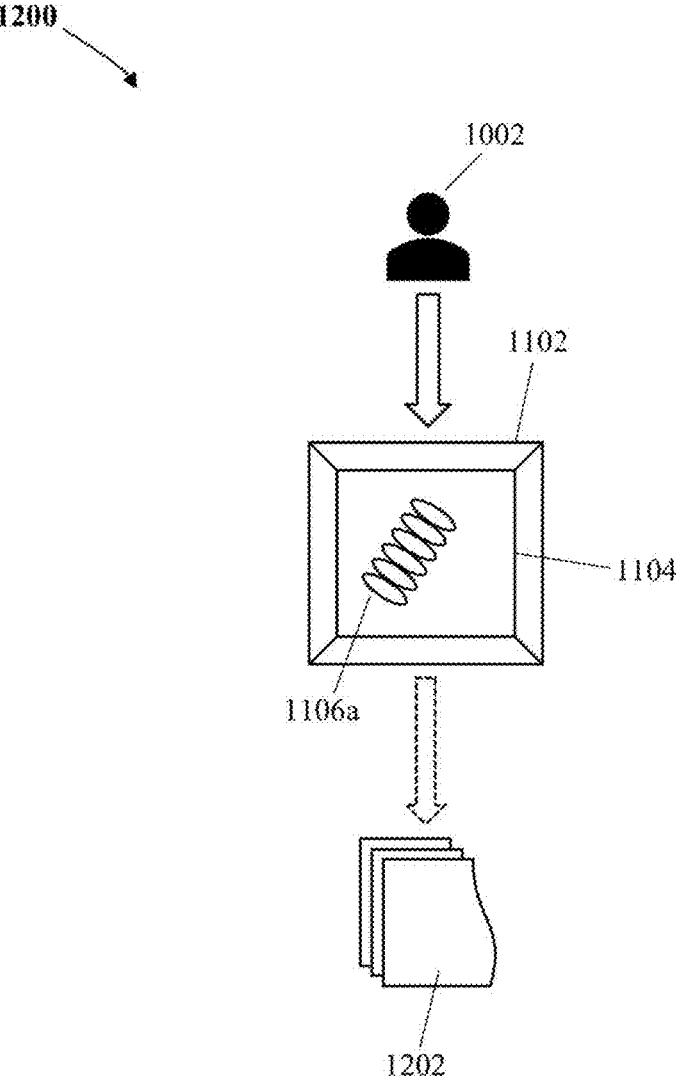
FIG. 7 is a schematic diagram of an aspect of the cognitive platform of the present disclosure, in accordance with an embodiment.

FIG. 7 is a schematic diagram of a routine 1200 for determining a measure of engagement for a user of a cognitive platform in accordance with an effort metric. In accordance with certain embodiments, one or more effort metric data 1202 is generated by mobile device 1102 (as shown in FIG. 6) from a user 1002 (as shown in FIG. 5). In various implementations, effort metric data 1202 is derived from analyzing patterns of user generated data from user 1002 via one or more said non-linear computational framework. In various embodiments, using effort metric data 1202, one or more training data set are derived to identify, quantify, or qualify one or more user characteristics including but not limited to effort or level of engagement, attention to tasks or user prompts, level of interaction/response time, level of skills, reaction time, cognitive function, memory, degeneration, improvement, cognitive deficit, plasticity, or the like. In various embodiments, effort metric data 1202 enables the classification or segmentation of one or more user 1002 via one or more said non-linear computational framework. In various embodiments, effort metric data 1202 enables the modification or adjustment, rate, frequency, or the like, of one or more graphical element/output/stimuli 1106a of FIG. 6 and associated computerized stimuli or interaction. In a non-limiting example, effort metric data 1202 enables the transition of graphical element/output/ stimuli 1106a into graphical element/output/stimuli 1106b of FIG. 6 or vice versa depending on the associated computerized stimuli or user interaction. In a non-limiting example, effort metric data 1202 enables the transition of the state or instance of at least one graphical element/output/ stimuli 1106a into the state or instance of at least one alternative graphical element/output 1106b of FIG. 6 or vice versa depending on the associated computerized stimuli or user interaction.

In one illustrative example, graphical element/output/ 1106b produces a second or subsequent plurality of effort metric data 1202. The computing device 1102 is configured to present the different types of interference as CSIs or other interactive elements that divert the user's attention from a primary task. For a distraction, the computing device 1102 is configured to instruct the individual to provide a primary response to the primary task and not to provide a response (i.e., to ignore the distraction). For an interrupter, the computing device is configured to instruct the individual to provide a response as a secondary task, and the computing device 1102 is configured to obtain data indicative of the user's secondary response to the interrupter within a short time frame as the user's response to the primary task thus generating effort metric data 1202. This enables computing device 1102 to compute measures of one or more of a user's performance at the primary task without an interference, performance with the interference being a distraction, and performance with the interference being an interruption. Then user's performance metrics can be computed based on these measures. For example, the user's performance, performance, engagement, or adherence to one or more tasks can be computed as a cost (performance change) for each type of interference (e.g., distraction cost and interrupter/ multi-tasking cost). The user's performance level on the tasks can be analyzed and reported as feedback, including either as feedback to the cognitive platform for use to adjust the difficulty level of the tasks, and/or as feedback to the individual concerning the user's status or progression, performance, engagement, or adherence, adjust types of tasks, and/or as feedback to the individual concerning the user's interaction with the computing device.

Figure 8:
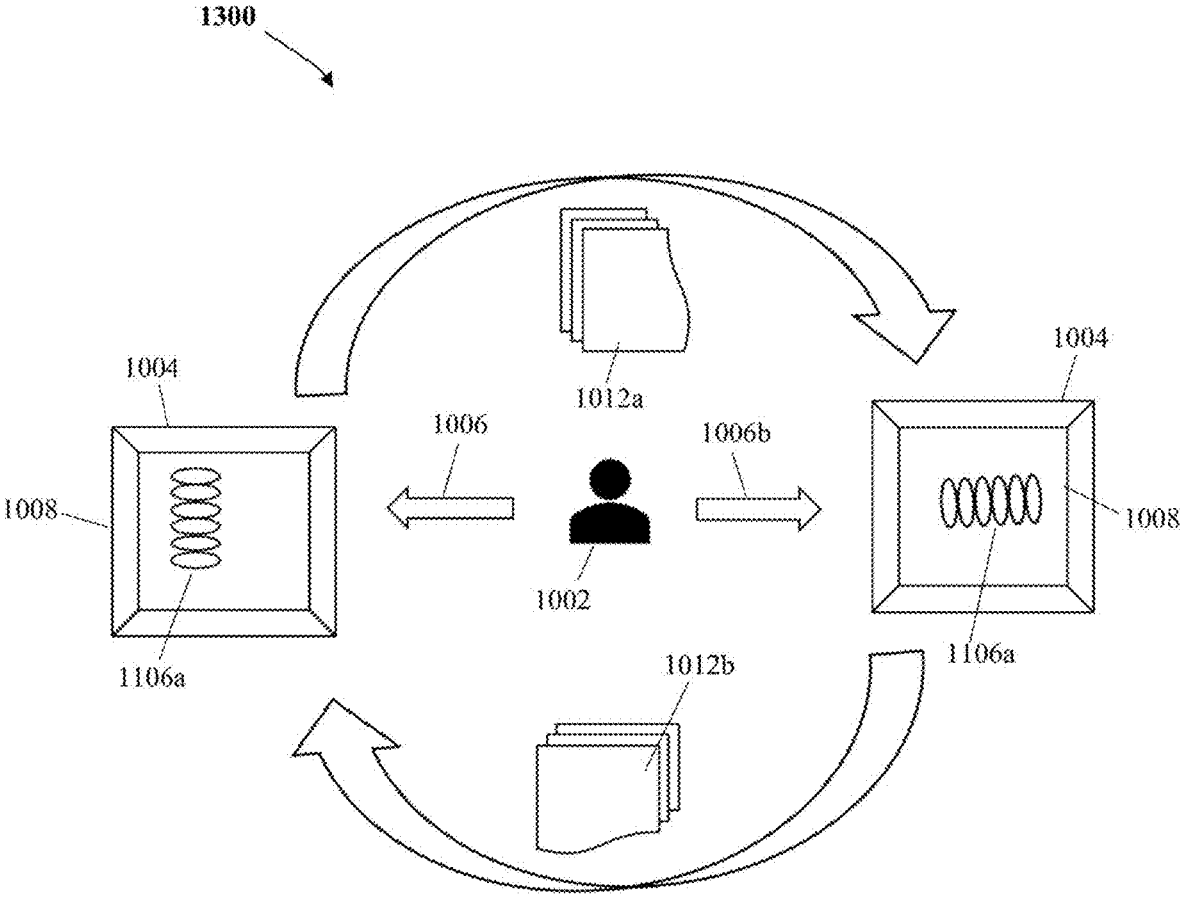
FIG. 8 is a schematic diagram of an aspect of the cognitive platform of the present disclosure, in accordance with an embodiment.

FIG. 8 is a schematic diagram of a routine 1300 for modifying and/or delivering one or more user interface element to a user in response to a measure of engagement with a cognitive platform. One or more effort metric data 1012a is generated by mobile device 1004 of FIG. 5 from a user 1002 of FIG. 5. In various implementations, effort metric data 1012a is derived from analyzing patterns of user generated data from user 1002 via one or more said nonlinear computational framework. In various embodiments, effort metric data 1012a are derived from one or more user input 1006 of FIG. 5 to enables the modification or adjustment, rate, frequency, or the like, of one or more graphical element/output/stimuli 1106a of FIG. 6 and associated computerized stimuli or interaction. In one embodiment, feedback loop processing, execution, or computation is performed using computing device 1014 of FIG. 5. In an alternative embodiment, feedback loop processing, execution, or computation is performed using computing server 1016 of FIG. 5 or combinations of the said computing devices; sequential or parallel. In a non-limiting example, effort metric data 1012a enables the transition of graphical element/output/stimuli 1106a or a state or an instance into graphical element/output/stimuli 1106b of FIG. 6 or vice versa depending on the associated computerized stimuli or user interaction. In a similar manner, effort data 1302b is generated from user input 1006b which is dependent on an associated computerized stimuli or user 1002's interaction with mobile computing device 1004. In various implementations, the computerized graphical element or output rendered on graphical user interface 1008 is based on feedback using effort metric data and said non-linear computational framework to write, send, adjust, or modify a user interface element, user prompt, notification, message, visual element of varying shape, color, sizes, rendering of a graphical output, visual stimuli, computerized stimuli, or the like. In various implementations, the computerized graphical element or output rendered on graphical user interface 1008 is based on qualification, quantification, categorization, classification, or segmentation of effort metric, training data, skill, level of task difficulty, number of tasks, multi-task, level of engagement, or the like. In various implementations, the computerized graphical element or output rendered on graphical user interface 1008 is continuously modified or adaptively changed as to optimize a subjective degree of user engagement in a computerized therapeutic treatment regimen. In various implementations, the computerized graphical element or output rendered on graphical user interface 1008 is continuously changed or adaptively changed as to improve sensitivity, specificity, area-under-the-curve, or positive/negative predictive value of a diagnosis or prediction of a cognitive function. In various implementations, the metric effort data 1012a or 1012b is continuously collected and one or more historical, current, or predicted states are analyzed from various instances/sessions of the application for quantifying performance, engagement, or adherence to tasks or therapy. In various implementations, the graphical element/output/stimuli 1106a or 1106b is modified, preferably in a continuous mode, based on one or more said historical, current or predicted metric data set from various instances/sessions of the application and presented or rendered on graphical user interface 1008 for the purpose of optimizing the user's performance, level of effort, engagement, or adherence to tasks, where interface modifications is for user effort optimization, whereby user engagement has a positive impact on treatment efficacy.

In accordance with certain embodiments, the computing device may be configured to present the different types of interference as CSIs or other interactive elements that divert the user's attention from a primary task. For a distraction, the computing device is configured to instruct the individual to provide a primary response to the primary task and not to provide a response (i.e., to ignore the distraction). For an interrupter, the computing device is configured to instruct the individual to provide a response as a secondary task, and the computing device is configured to obtain data indicative of the user's secondary response to the interrupter within a short time frame (including at substantially the same time) as the user's response to the primary task (where the response is collected using at least one input device). The computing device is configured to compute measures of one or more of a user's performance at the primary task without an interference, performance with the interference being a distraction, and performance with the interference being an interruption. The user's performance metrics can be computed based on these measures. For example, the user's performance can be computed as a cost (performance change) for each type of interference (e.g., distraction cost and interrupter/multi-tasking cost). The user's performance level on the tasks can be analyzed and reported as feedback, including either as feedback to the cognitive platform for use to adjust the difficulty level of the tasks, and/or as feedback to the individual concerning the user's status or progression. In another example, the user's engagement or adherence level can be computed as a cost (performance change) for each type of interference (e.g., distraction cost and interruptor/multi-tasking cost). The user's engagement or adherence level on the tasks can be analyzed and reported as feedback, including either as feedback to the cognitive platform for use to monitor user's engagement or adherence, adjust types of tasks, and/or as feedback to the individual concerning the user's interaction with the computing device.

Referring now to FIG. 9, a process flow chart of a method 1400 for deriving an effort metric for optimizing user engagement in a cognitive platform is shown. In accordance with an embodiment, a cognitive platform comprises a mobile electronic device operably engaged with a local and/or remote processor(s), a memory device operably engaged with the processor, and a display component comprising an I/O device. In various embodiments, a cognitive platform comprises the apparatus and/or system as shown and described in FIGS. 1 and 2, above. In accordance with an embodiment of method 1400, a cognitive platform is configured to receive a first plurality of user data comprising a training dataset, the first plurality of user data comprising at least one user-generated input in response to a first instance of a computerized stimuli or interaction associated with a computerized therapeutic treatment regimen executing on a mobile electronic device 1402. The computerized stimuli or interaction may comprise one or more user tasks being displayed via a graphical user interface. By means of a non-limiting example of an illustrative embodiment, computerized stimuli or interaction may comprise a visuomotor or navigation task to be performed in the presence of one or more secondary or distractor tasks. In accordance with certain embodiments, the user may provide one or more sensor inputs via a mobile electronic device in response to the computerized stimuli or interaction to be received by the processor, which may optionally be stored in a local or remote memory device comprising one or more databases. In response to receiving the first plurality of user data (e.g. training dataset), method 1400 may further be configured to compute, with the processor, the first plurality of user data according to a non-linear computational framework to derive an effort metric based on one or more user response patterns to the computerized stimuli or interaction 1404. In accordance with various embodiments, the non-linear computational framework may comprise an artificial neural network; for example, a convolutional neural network or a recurrent neural network. The non-linear computational framework may be configured to apply one or more deep learning techniques to the first plurality of user data to derive patterns from the sensor inputs and/or other user-generated inputs being indicative of the user responses to the stimuli and the temporal relationship of the sensor measurement of the user responses to the stimuli. The non-linear computational framework may characterize the derived patterns of the user responses to the stimuli to define an effort metric, the effort metric being correlated to patterns of user inputs indicative of a level of user engagement or user effort being applied by the user in connection with an instance or session of the computerized therapeutic treatment regimen.

Upon calculating the effort metric from the first plurality of user data, method 1400 may further be configured to receive at least a second plurality of user data comprising at least one user-generated input in response to at least a second instance of the computerized stimuli or interaction 1406. In accordance with various embodiments, the second plurality of data comprises sensor inputs and/or other user-generated inputs corresponding to a second instance or session, and/or one or more subsequent instances or sessions, with the computerized therapeutic treatment regimen. Upon receiving the second or subsequent plurality of user data, method 1400 may further be configured to compute or analyze the second plurality of user data according to the non-linear computational framework to determine a quantified measure of user engagement associated with the second instance of the computerized stimuli or interaction based on the effort metric 1408. The second or subsequent plurality of user data may be computed or analyzed in real-time, at pre-determined time intervals or conditions, or on an ad hoc basis in response to a user query or request to determine the measure of user engagement. Embodiments of the cognitive platform may be further configured to analyze or apply the quantified measure of user engagement to a specified engagement/effort threshold or trigger value or a pre-determined or adaptive range or spectrum of values corresponding to a characterization of measure of user engagement (e.g., insufficient effort, sufficient effort, optimal effort). In certain embodiments, in response to the quantified measure of user engagement, method 1400 may further be configured to modify, adapt or deliver at least one user interface element or user prompt associated with the second instance or subsequent instance of the computerized stimuli or interaction in response to the measure of user engagement 1410. Method 1400 may be configured to modify, adapt or deliver at least one user interface element or user prompt 1410 in response to the quantified measure of user engagement being below the specified threshold or trigger value and/or in accordance with the adaptive range or spectrum of effort/engagement characterization(s). Illustrative examples of user prompts or user interface elements may include one or more or a combination of: a text or audio notification, message and/or alert; modification of a graphical element in the user interface; modification of the presentment of the order, timing, orientation, design, organization, and/or display of one or more graphical elements in the user interface; a haptic output, such as a vibrational output; addition of one or more user interface elements, such as additional screens, game elements, or game levels; and the overlay of one or more additional user interface elements, such as one or more message, character, or game element.

Referring now to FIG. 10, a process flow chart of a method 1500 for deriving an effort metric for optimizing user engagement in a cognitive platform is shown. Method 1500 may comprise further process steps in the continuance of method 1400. In accordance with an embodiment, method 1500 may be configured to receive a third or subsequent plurality of user data from the mobile electronic device, the third or subsequent plurality of user data comprising user-generated inputs in response to a third or subsequent instance of the computerized stimuli or interaction comprising and/or in the presence of the modified user interface element(s) or user prompt(s) 1502. Method 1500 may be further configured to compute the third or subsequent plurality of user data according to the non-linear computational framework to determine a measure of user engagement associated with a third or subsequent instance of the computerized stimuli or interaction based on the effort metric 1504. Method 1500 may be further configured to further modify, adapt, or deliver at least one user interface element or user prompt to the mobile electronic device in response to the measure of user engagement being below a specified threshold value, the at least one user interface element or user prompt comprising a task or instruction associated with the computerized therapeutic treatment regimen 1506. In accordance with certain embodiments, method 1500 may comprise an adaptive feedback loop generally comprising the steps of (a) monitoring/receiving user generated data from an $N^{th}$ instance or session of the computerized stimuli or interaction comprising a modified or adapted user interface element(s); (b) calculating or analyzing an $N^{th}$ measure of user engagement for the $N^{th}$ instance or session of the computerized stimuli or interaction; and, (c) further modifying or adapting the user interface element(s) for presentment or display in a subsequent instance or session of the computerized stimuli. In accordance with certain embodiments, method 1500 may be further optionally configured to calculate a correlation between user engagement data and efficacy metrics 1508 to render one or more real-time or ad hoc outputs, the outputs comprising one or more usage insights, graphical reports, and/or data visualizations corresponding to user trends, therapeutic efficacy, user improvement in on or more CSIs or other metrics, and use-based metrics. Method 1500 may further comprise communicating or delivering the one or more real-time or ad hoc outputs to one or more external or third-party user devices or external applications, such as a caregiver client device/application, a medical practitioner client device/application, or a payer client device/application. In certain embodiments, one or more external or third-party user devices or external applications may enable one or more external or third-party users to monitor and view treatment adherence, treatment efficacy, and treatment outcomes for the patient-user.

Figure 11:
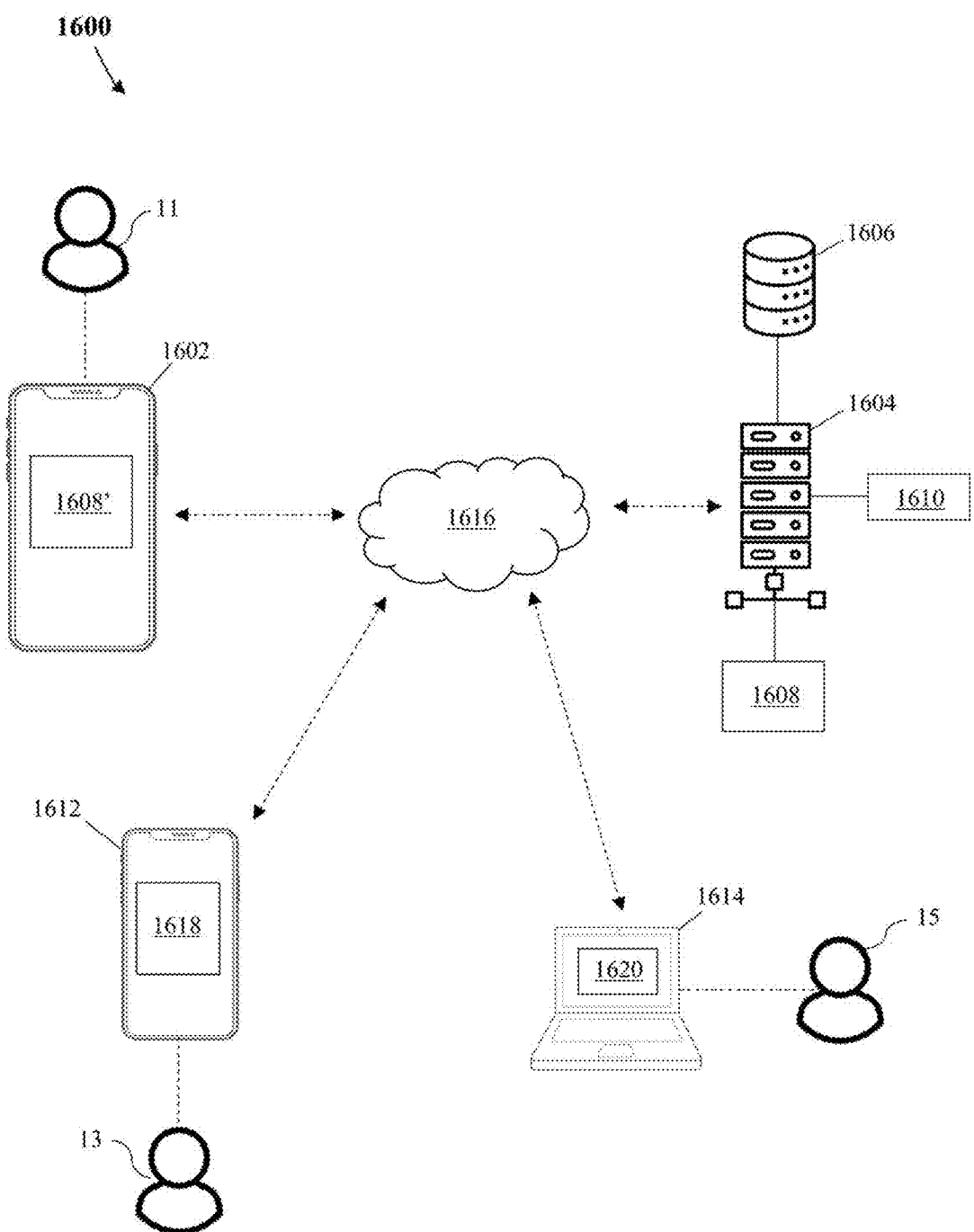
FIG. 11 is an architecture diagram of a multi-user cognitive training system, in accordance with certain aspects of the present disclosure.

Referring now to FIG. 11, an architecture diagram of a multi-user cognitive training system 1600 is shown. In accordance with certain aspects of the present disclosure, system 1600 may comprise or be embodied by one or more steps, operations, components or methods shown and described in FIGS. 1-10. In accordance with certain aspects of the present disclosure, system 1600 may be configured to process user activity data for a first end user of a first user application according to at least one machine learning model and configure/render one or more user interface elements at a graphical user interface of a second user application according to one or more model outputs for the at least one machine learning model. In accordance with certain aspects of the present disclosure, system 1600 may comprise an end user device 1602, a companion user device 1612, an admin client device 1614 and an application server 1604. Each of end user device 1602, companion user device 1612 and admin client device 1614 may be communicably engaged with application server 1604 via network interface 1616. In accordance with certain embodiments, network interface 1616 may enable a real-time data transfer interface between end user device 1602, companion user device 1612, admin client device 1614 and application server 1604. System 1600 may further comprise an application database 1606 communicably engaged with application server 1604. In accordance with certain embodiments, application server 1604 may comprise a machine learning (ML) engine 1610 and a cognitive training application 1608 embodied as one or more processor-executable instructions stored in a non-transitory computer readable medium contained thereon.

In accordance with certain aspects of the present disclosure, an end user instance 1608' of cognitive training application 1608 may be configured to present one or more computerized stimuli or interactions comprising one or more cognitive training tasks to an end user 11 at a graphical user interface of end user device 1602. The one or more cognitive training tasks may comprise one or more time-varying computerized tasks configured to elicit one or more desired or pre-determined stimulus-response patterns from end user 11. In accordance with certain embodiments, the one or more computerized tasks may comprise one or more navigation, target discrimination and/or visuomotor tracking tasks. In certain embodiments, end user instance 1608' is configured to elicit, and end user device 1602 is configured to receive via one or more sensors, one or more user-generated inputs at the user interface of end user device 1602. In certain embodiments, the one or more user-generated inputs may comprise one or more physical inputs such as tapping/touching the screen of end user device 1602 and/or turning or moving end user device 1602 in a specified direction (e.g., up, down, left, right). In accordance with certain aspects of the present disclosure, end user 11 may engage with one or more sessions of cognitive training application 1608 via end user instance 1608' over a specified time period (e.g., 5 days, 10 days, 14 days, 21 days, one month, two months, etc.). End user instance 1608' may receive the one or more user-generated inputs from end user 11 at the user interface of end user device 1602 across the one or more sessions of cognitive training application 1608 and communicate user-activity data comprising the one or more user-generated inputs to application server 1604 via network interface 1616.

In accordance with certain aspects of the present disclosure, application server 1604 may provide the user activity data to ML engine 1610 for processing according to at least one machine learning model. In accordance with certain aspects of the present disclosure, the machine learning model may comprise a classification model comprising one or more ensemble framework. The classification model may comprise one or more random forest algorithm or random decision forest algorithm configured to classify one or more variables in the user activity data to label one or more characteristics (i.e., variables) within the user activity data. In accordance with certain aspects of the present disclosure, ML engine 1610 is configured to label one or more characteristics (i.e., variables) associated with a level of user effort exhibited by end user 11 during each session of cognitive training application 1608. For example, the one or more characteristics (i.e., variables) may be associated with one or more desired stimulus-response pattern for the one or more computerized tasks; for example, percentage of correct responses and/or percentage of responses within time window. In accordance with certain aspects of the present disclosure, a model output of ML engine 1610 may comprise one or more characteristics associated with a level of user effort exhibited by end user 11 during each session of cognitive training application 1608. Application server 1604 may be configured to store the model output and the user activity data in application database 1606.

In accordance with certain aspects of the present disclosure, companion user device 1612 may comprise an instance of a companion application 1618 executing thereon. Companion application 1618 may be a companion application of cognitive training application 1608. Application server 1604 may be configured to execute one or more operations for linking a first user profile for end user 11 with a second user profile for a companion user 13 (e.g., a parent user, a caregiver user, and/or a healthcare practitioner user) in application database 1606. In certain embodiments, the one or more operations for linking the first user profile for end user 11 with a second user profile for companion user 13 may include one or more data transfer permissions/protocols for sharing user activity data between end user 11 and companion user 13. In accordance with certain aspects of the present disclosure, companion application 1618 may be configured to process one or more model outputs associated with one or more sessions of end user instance 1608' in order to render one or more graphical user interface elements at the instance of companion application 1618. In accordance with certain embodiments, the one or more graphical user interface elements may comprise one or more visualizations of the model output for ML engine 1610 for one or more sessions of cognitive training application 1608. In certain embodiments, companion application 1618 may comprise one or more interface elements configured to enable companion user 13 to query the model output for ML engine 1610 for one or more current or historical sessions of cognitive training application 1608. In certain embodiments, one or more graphical user interface elements of companion application 1618 may be updated or modified in real-time in response to end user 11 completing one or more sessions of companion application 1618.

In accordance with certain aspects of the present disclosure, system 1600 may comprise at least one administrator client device 1614 communicably engaged with application server 1604 via network interface 1616. Administrator client device 1614 may comprise an administrator application 1620 being executed thereon. Administrator application 1620 may be an administrator application for cognitive training application 1608; for example, a payor application or a healthcare practitioner application. Application server 1604 may be configured to execute one or more operations for linking the first user profile for end user 11 with a third or subsequent user profile for an administrator user 15 (e.g., a payor user or a healthcare practitioner user) in application database 1606. In certain embodiments, the one or more operations for linking the first user profile for end user 11 with the third user profile for administrator user 15 may include one or more data transfer permissions/protocols for sharing user activity data between end user 11 and administrator user 15. In accordance with certain aspects of the present disclosure, administrator application 1620 may be configured to receive/process one or more model outputs associated with one or more sessions of end user instance 1608' in order to render one or more graphical user interface elements at the instance of administrator application 1620. In accordance with certain embodiments, the one or more graphical user interface elements may comprise one or more visualizations of the model output for ML engine 1610 for one or more sessions of cognitive training application 1608 (including visualizations for one or more user outcomes or statistics). In certain embodiments, administrator application 1620 may comprise one or more interface elements configured to enable administrator user 15 to query the model output for ML engine 1610 for one or more current or historical sessions of cognitive training application 1608. In certain embodiments, one or more graphical user interface elements of administrator application 1620 may be updated or modified in real-time in response to end user 11 completing one or more sessions of companion application 1618.

Figure 12:
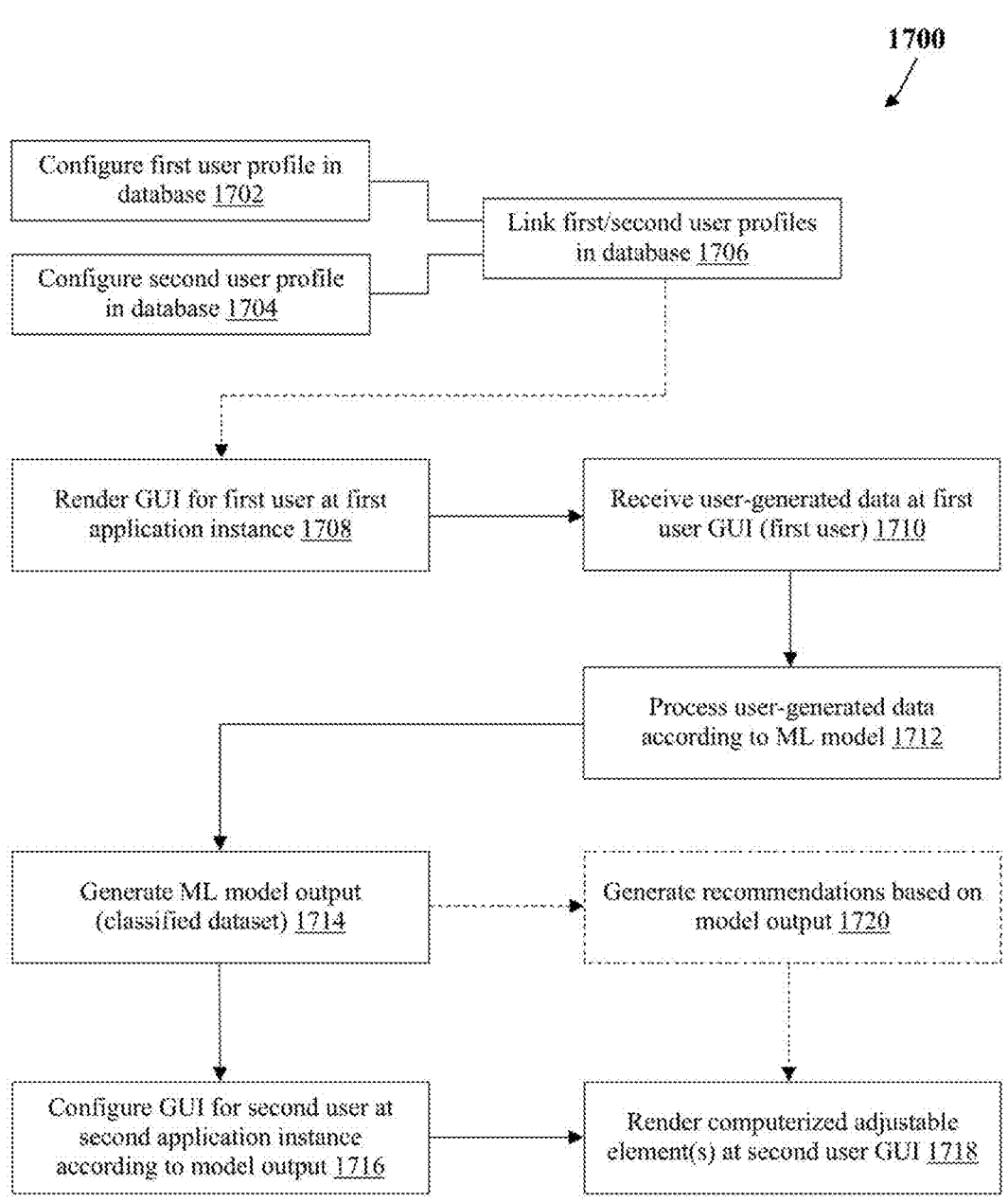
FIG. 12 is a routine of a multi-user cognitive training system, in accordance with certain aspects of the present disclosure.

Referring now to FIG. 12, a routine 1700 of a multi-user cognitive training system is shown. In accordance with certain aspects of the present disclosure, routine 1700 may be embodied as an operational routine within one or more components of system 1600, as shown in FIG. 11. In accordance with certain aspects of the present disclosure, routine 1700 may comprise one or more steps or operations for configuring a first user profile for a first user of a cognitive training application in an application database (Step 1702) and configuring a second user profile for a second user of the cognitive training application in the application database (Step 1704). The first user profile may be associated with an end user of the cognitive training application (i.e., a patient or a training subject). The second user profile may be associated with a companion user associated with the end user of the cognitive training application (e.g., a parent or guardian of the end user). Routine 1700 may continue by performing one or more steps or operations for linking the first user profile and the second user profile in the application database (Step 1706). In certain embodiments, step 1706 may comprise one or more operations for establishing one or more data transfer interface and/or data access permissions between the first user profile and the second user profile (e.g., visibility and/or access to user activity data generated at the first user profile by the second user profile). In accordance with certain aspects of the present disclosure, steps 1702-1706 may occur one time; e.g., as part of an account setup interface/workflow. Routine 1700 may proceed by executing one or more steps or operations for rendering a graphical user interface (GUI) for the first user at a first instance of the cognitive training application (Step 1708). In accordance with certain embodiments, the GUI may comprise one or more CSIs comprising one or more computerized cognitive training tasks configured to prompt a time-dependent response from the user. Routine 1700 may continue by receiving one or more user-generated responses to the one or more CSIs from the first user via the first instance of the cognitive training application (i.e., user activity data) at the application server (Step 1710). In accordance with certain aspects of the present disclosure, the one or more user-generated responses may comprise signal data received by one or more sensors of an end user device. Routine 1700 may proceed by executing one or more steps or operations for processing the user activity data according to a ML model to classify one or more variables and/or response patterns within the user activity data (Step 1712). In certain embodiments, the ML model may comprise at least one ensemble machine learning framework comprising one or more random forest or random decision tree forest algorithms. Routine 1700 may proceed by executing one or more steps or operations for generating an output for the ML model comprising a classified (e.g., labeled) dataset for the user activity data (Step 1714). In accordance with certain embodiments, the ML model may be configured to generate one or more recommendations based on the model output (Step 1720). The model output may be configured to classify one or more performance metrics associated with one or more measure (i.e., degree) of user effort for the first user during the session of the cognitive training application. The one or more recommendations may comprise one or more recommendations for improving the one or more performance metrics for the first user in one or more subsequent sessions of the cognitive training application. In certain embodiments, the ML model is configured to generate the one or more recommendations according to at least one supervised learning model or unsupervised learning model (e.g., an artificial neural network). In accordance with certain aspects of the present disclosure, routine 1700 may proceed by performing one or more steps or operations for processing the model output at the application server to configure a graphical user interface for the second user at a second instance of the cognitive training application (Step 1716). In accordance with certain aspects of the present disclosure, the second instance of the cognitive training application comprises a companion application to the cognitive training application. In accordance with certain aspects of the present disclosure, routine 1700 may proceed by executing one or more steps or operation for rendering one or more computerized adjustable elements at the graphical user interface for the second user at a second instance of the cognitive training application (i.e., the companion application) (Step 1718). In accordance with certain embodiments, the computerized adjustable elements comprise one or more graphical elements configured to visualize one or more performance metrics for the end user according to the model output. The computerized adjustable elements may be dynamically adjusted or modified to represent a degree of user effort for the end user for the session or grouping of sessions of the cognitive training application according to the model output. According to certain embodiments, the graphical user interface for the companion application may comprise one or more elements configured to enable the second user to query historical user activity data for the first user in the application database. The graphical user interface for the companion application may comprise one or more elements configured to enable the second user to query one or more aspects of the model output for the first user in the application database. The graphical user interface for the companion application may comprise one or more elements for providing one or more recommendations for the second user to improve the performance (i.e., level of effort) for the first user.

Figure 13:
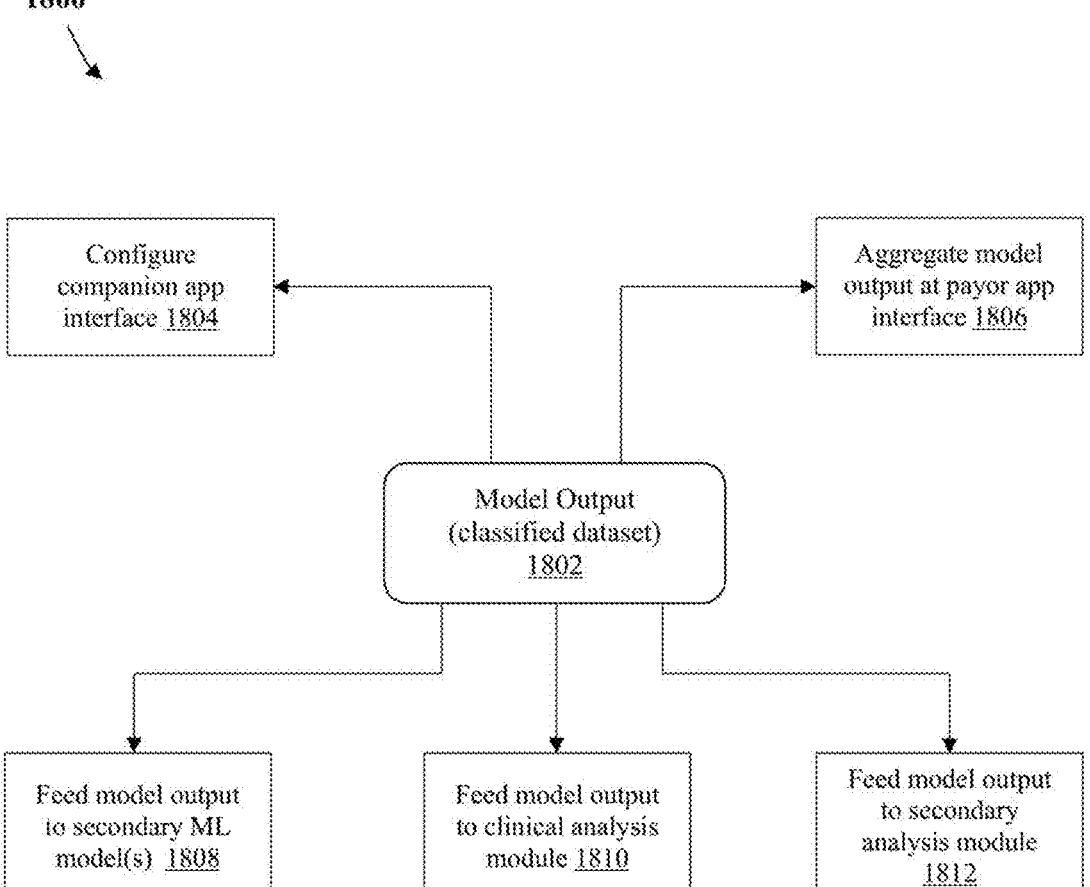
FIG. 13 is a routine of a multi-user cognitive training system, in accordance with certain aspects of the present disclosure.

Referring now to FIG. 13, a routine 1800 of a multi-user cognitive training system is shown. In accordance with certain aspects of the present disclosure, routine 1800 may be embodied as an operational routine within one or more components of system 1600, as shown in FIG. 11. In certain embodiments, routine 1800 may be successive or sequential to one or more steps or operations of routine 1700, as shown in FIG. 12, and/or may comprise one or more sub-steps or sub-routines of routine 1700. In accordance with certain aspects of the present disclosure, routine 1800 may comprise a data flow of a model output 1802 of a machine learning engine (e.g., ML engine 1610 of FIG. 11) comprising a classified dataset of user activity data from one or more sessions of the cognitive training application to the end user (e.g., end user instance 1608' of FIG. 11). In accordance with certain aspects of the present disclosure, routine 1800 may comprise one or more steps or operations for processing the model output 1802 of the machine learning engine according to one or more of steps 1804-1812. In accordance with certain aspects of the present disclosure, routine 1800 may comprise one or more steps or operations for processing (e.g., with application server 1604 of FIG. 11) the model output 1802 in order to configure 1804 an instance of a companion application (e.g., companion application 1618 of FIG. 11) for the multi-user cognitive training system. In certain embodiments, step 1804 may comprise one or more operations for configuring one or more graphical user interface elements for the companion application according to the model output. The one or more graphical user interface elements may comprise one or more computerized adjustable element configured to display/visualize/illustrate a degree of user effort for the end user over one or more sessions of the cognitive training application. In accordance with certain aspects of the present disclosure, routine 1800 may comprise one or more steps or operations for processing (e.g., with application server 1604 of FIG. 11) the model output 1802 in order to aggregate 1806 one or more groups of classified data at a payor application interface (e.g., administrator application 1620 of FIG. 11) of the multi-user cognitive training system. The payor application interface may include one or more graphical elements configured to display/visualize/illustrate a progression of a degree of user effort for the end user across one or more sessions of the cognitive training application and/or a progression of performance (i.e., improvement) for the end user across the one or more sessions of the cognitive training application.

In accordance with certain aspects of the present disclosure, routine 1800 may comprise one or more steps or operations for communicating a feed (e.g., via a data transfer interface such as an API or an SDK) of the model output into one or more secondary ML models (Step 1808). In certain embodiments, the one or more secondary ML models may comprise one or more ML models for monitoring, improving, adaptively modifying and/or configuring one or more aspects of the cognitive training application; for example, a degree of difficulty of the cognitive training application (e.g., a response deadline or speed of an object) or a visual appearance of one or more graphical elements of the cognitive training application. In certain embodiments, routine 1800 may comprise one or more steps or operations for communicating a feed (e.g., via a data transfer interface such as an API or an SDK) of the model output into one or more clinical analysis module (Step 1810) (e.g., executing on application server 1604 of FIG. 11). In certain embodiments, the clinical analysis module may be configured to analyze the user activity data and/or the model output to determine one or more safety, efficacy and/or performance metrics for the cognitive training application. In certain embodiments, routine 1800 may comprise one or more steps or operations for communicating a feed (e.g., via a data transfer interface such as an API or an SDK) of the model output into one or more secondary analysis module (Step 1812) (e.g., executing on application server 1604 of FIG. 11). In certain embodiments, the secondary analysis module may be configured to analyze the user activity data and/or the model output to conduct one or more secondary analysis for the cognitive training application; for example, an analysis to determine the impact of one or more aspects of the cognitive training application on the level of effort of the end user across the one or more sessions of the cognitive training application.

Figure 14:
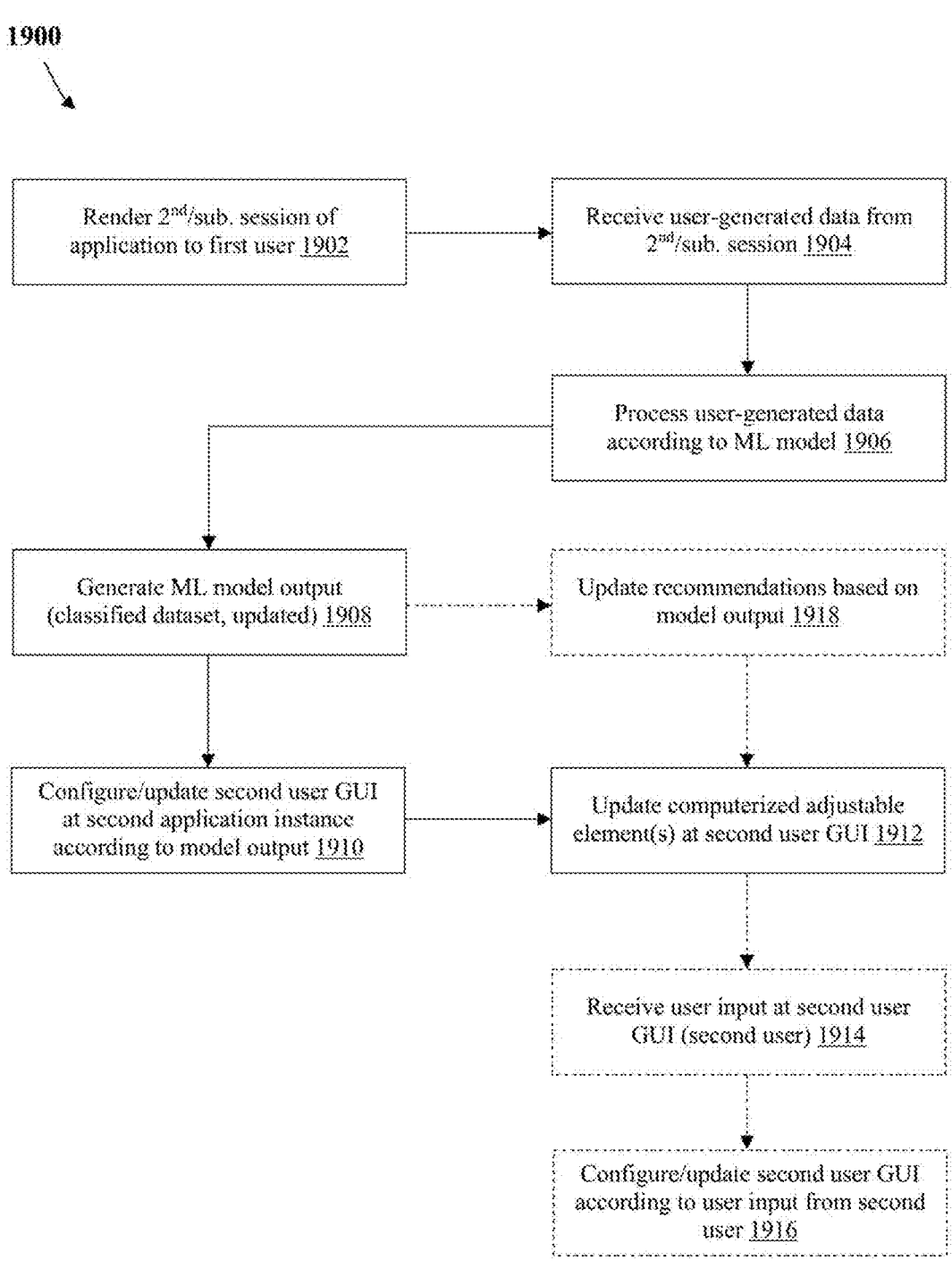
FIG. 14 is a routine of a multi-user cognitive training system, in accordance with certain aspects of the present disclosure.

Referring now to FIG. 14, a routine 1900 of a multi-user cognitive training system is shown. In accordance with certain aspects of the present disclosure, routine 1900 may be embodied as an operational routine within one or more components of system 1600, as shown in FIG. 11. In certain embodiments, routine 1900 may be successive or sequential to one or more steps or operations of routine 1700 and/or routine 1800, as shown in FIGS. 12-13, and/or may comprise one or more sub-steps or sub-routines of routine 1700 and/or routine 1800. In accordance with certain aspects of the present disclosure, routine 1900 may proceed by executing one or more steps or operations for rendering a second or subsequent session of the cognitive training application to the first user at the end user device (Step 1902). Routine 1900 may continue by receiving (e.g., at the application server) one or more user-generated responses to one or more CSIs presented at the second or subsequent instance of the cognitive training application from the first user via the second or subsequent instance of the cognitive training application (Step 1904). In accordance with certain aspects of the present disclosure, the one or more user-generated responses may comprise signal data received by the one or more sensors of the end user device. Routine 1900 may proceed by executing one or more steps or operations for processing the user activity data according to the ML model to classify one or more variables and/or response patterns within the user activity data (Step 1906). Routine 1900 may proceed by executing one or more steps or operations for generating an output for the ML model comprising a classified (e.g., labeled) dataset for the user activity data (Step 1908). In accordance with certain embodiments, the ML model may be configured to update the one or more recommendations based on the model output (Step 1918). In accordance with certain aspects of the present disclosure, routine 1900 may proceed by performing one or more steps or operations for processing the model output (e.g., at the application server) to configure/update the graphical user interface for the second user at the second instance of the cognitive training application (Step 1912). In accordance with certain aspects of the present disclosure, routine 1900 may proceed by executing one or more steps or operation for updating or modifying the one or more computerized adjustable elements at the graphical user interface for the second user at the second instance of the cognitive training application (Step 1912). In accordance with certain aspects of the present disclosure, the second instance of the cognitive training application may comprise a companion application of the cognitive training application (e.g., companion application 1618 of FIG. 11). In accordance with certain embodiments, the computerized adjustable elements comprise the one or more graphical elements configured to visualize one or more performance metrics for the end user according to the model output. Step 1912 may comprise one or more operations for dynamically adjusting or modifying the computerized adjustable element to represent a degree of user effort for the end user for the second or subsequent sessions of the cognitive training application according to the model output. The graphical user interface for the companion application may comprise one or more elements for providing one or more recommendations for the second user to improve the performance (i.e., level of effort) for the first user across the second or subsequent sessions of the cognitive training application. In accordance with certain aspects of the present disclosure, routine 1900 may proceed by executing one or more steps or operation for receiving a user-generated input from the second user at the graphical user interface of the second instance of the cognitive training application (Step 1914). In accordance with certain embodiments, the user-generated input may comprise a query or a selection to view one or more data visualizations related to the level of effort or performance of the first user. Routine 1900 may proceed by executing one or more steps or operation for configuring or updating the graphical user interface of the second instance of the cognitive training application in response to receiving/processing the user-generated input from the second user (Step 1916).

Figure 15A:
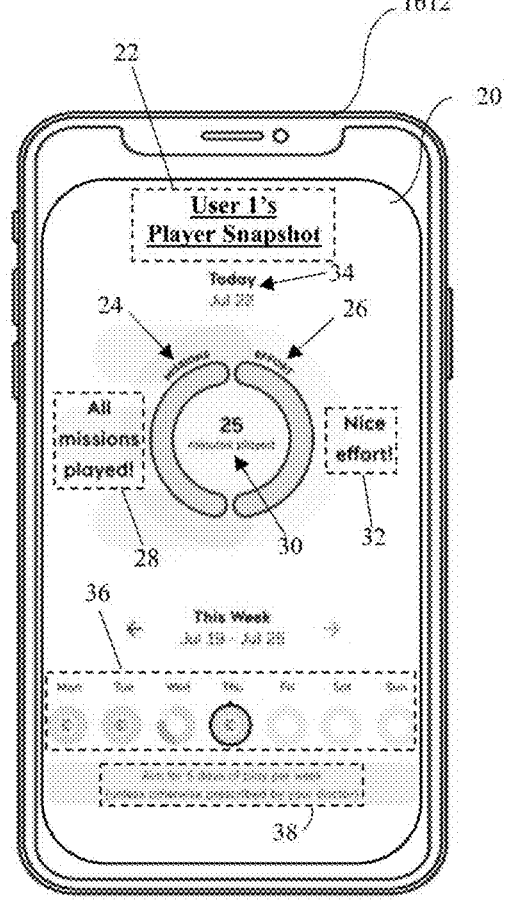
FIGS. 15A and 15B are graphical illustrations of a user interface for a companion application within a multi-user cognitive training system.
Figure 15B:
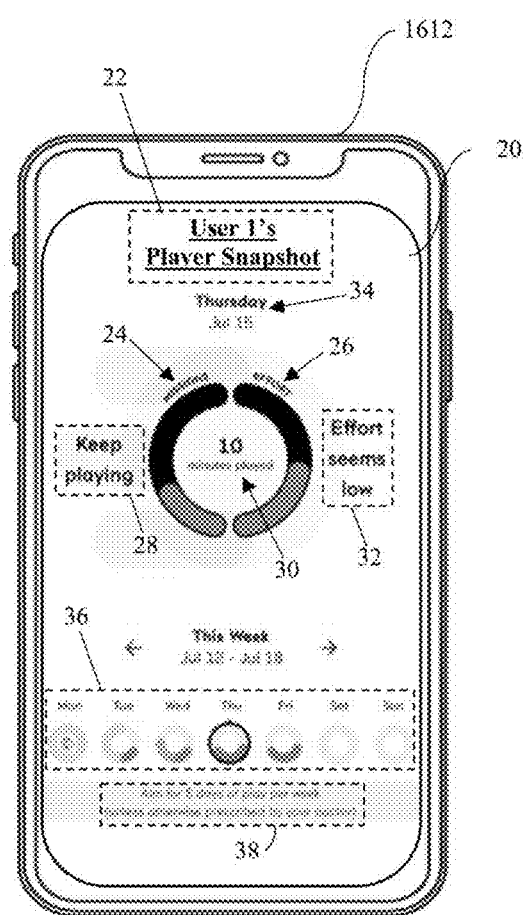

FIGS. 15A and 15B are graphical illustrations of a user interface 20 for a companion application (e.g., companion application 1618 of FIG. 11) within a multi-user cognitive training system (e.g., system 1600 of FIG. 11). In accordance with certain aspects of the present disclosure, user interface 20 may be rendered at a display of companion user device 1612 to a companion user (e.g., companion user 13 in FIG. 12). In certain embodiments, user interface 20 may comprise user interface elements 22-38. A first user interface element 22 may comprise a display of the linked end user for the companion user account. A second user interface element 24 may comprise a first computerized adjustable element configured to display an indication of a number of sessions of the cognitive training application completed by the linked end user for a specified time period. As shown in FIG. 15B, second user interface element 24 may be dynamically rendered according to the session data for the linked end user stored in the application database. A third user interface element 26 may comprise a second computerized adjustable element. In accordance with certain embodiments, the second computerized adjustable element may be configured to display a qualitative measure of user engagement across one or more sessions of the cognitive training application. In accordance with certain aspects of the present disclosure, third user interface element 26 may be configured according to an output of an ML model (e.g., model output for ML engine 1610). A fourth user interface element 28 may comprise an indication of a number of sessions of the cognitive training application over a specified time period. In accordance with certain embodiments, a target number of sessions for a specified time period is configured for the linked end user; for example, 5 sessions over a 7-day period. Fourth user interface element 28 may be configured based on user activity data for the linked end user in the application database (e.g., application database 1606). As shown in FIG. 15B, fourth user interface element 28 may be configured to provide an indication to the companion user that the linked end user has not completed the target sessions of the specified time period. A fifth user interface element 30 may comprise an indication of a time period during which the linked end user has engaged with the cognitive training application over a specified time period. Fifth user interface element 30 may be configured based on user activity data for the linked end user in the application database. A sixth user interface element 32 may be configured to provide an indication to the companion user that a degree of effort for the linked end user is at or below a target threshold based on the ML model output. A sixth user interface element 34 may be configured to display a date for the completed session or sessions of the cognitive training application for the linked end user being rendered at user interface 20. A seventh user interface element 36 may be configured to display a date range for one or more completed sessions of the cognitive training application for the linked end user being rendered at user interface 20. An eighth user interface element 38 may comprise a target number of sessions (i.e., dosing) for the linked end user over a specified time period.

Referring now to FIG. 16, a process flow diagram of a method 2100 for configuring a user interface for a companion application within a multi-user cognitive training system is shown. In accordance with certain aspects of the present disclosure, method 2100 may be embodied as one or more routines 1700-1900, as shown in FIGS. 12-14, of a multi-user cognitive training system (e.g., multi-user cognitive training system 1600, as shown in FIG. 11). In accordance with certain aspects of the present disclosure, method 2100 may be initiated upon performing one or more steps or operations for configuring (e.g., with application server 1604 of FIG. 11) an instance of a cognitive training application for a first end user and an instance of a companion application for the cognitive training application for a second end user (Step 2102). Method 2100 may proceed be performing one or more steps or operations for linking (e.g., with the application server) the first end user and the second end user in an application database (e.g., application database 1606 of FIG. 11) (Step 2104). In accordance with certain aspects of the present disclosure, linking the first end user and the second end user comprises enabling at least one data transfer interface between the cognitive training application and the companion application. Method 2100 may proceed by performing one or more steps or operations for presenting (e.g., with a first end user computing device communicably engaged with the application server) the instance of the cognitive training application to the first end user (Step 2106). In accordance with certain aspects of the present disclosure, the instance of the cognitive training application comprises one or more computerized stimuli or interactions configured to elicit a specified response from the first end user, wherein the specified response comprises a time-varying response deadline. Method 2100 may proceed by performing one or more steps or operations for receiving (e.g., with the application server) a plurality of user activity data comprising a plurality of user-generated responses by the first end user to the one or more computerized stimuli or interactions presented during the instance of the cognitive training application (Step 2108). Method 2100 may proceed by performing one or more steps or operations for processing (e.g., with the application server) the plurality of user activity data according to a machine learning framework (Step 2110). In accordance with certain aspects of the present disclosure, the machine learning framework comprises an ensemble learning model comprising at least one random decision forest algorithm. In accordance with certain aspects of the present disclosure, the machine learning framework is configured to classify one or more stimulus-response patterns from the plurality of user activity data to generate a classified dataset comprising one or more data labels for one or more attributes of the plurality of user activity data. Method 2100 may proceed by performing one or more steps or operations for storing (e.g., with the application server) the classified dataset in the application database (Step 2112). Method 2100 may proceed by performing one or more steps or operations for presenting (e.g., with a second end user computing device communicably engaged with the application server) the instance of the companion application for the cognitive training application to the second end user (Step 2114). Method 2100 may proceed by performing one or more steps or operations for fetching (e.g., with the instance of the companion application via the application server) one or more datapoints from the classified dataset in the application database (Step 2116). Method 2100 may proceed by performing one or more steps or operations for configuring or modifying (e.g., with the instance of the companion application) one or more graphical user interface elements for the companion application according to the one or more datapoints from the classified dataset (Step 2118). Method 2100 may proceed by performing one or more steps or operations for presenting (e.g., with the instance of the companion application) the one or more graphical user interface elements to the second end user (Step 2120). In accordance with certain embodiments, the one or more graphical user interface elements comprise at least one computerized adjustable element configured to provide one or more quantitative metrics for the first end user according to the classified dataset.

In accordance with certain aspects of method 2100, the one or more quantitative metrics comprise a quantified number of sessions of the cognitive training application for the first end user for a specified time period. In certain embodiments, the one or more quantitative metrics comprise a measure of user engagement for the first end user during the quantified number of sessions. In certain embodiments, the at least one computerized adjustable element is configured to indicate an amount of time the first end user engaged with the instance of the cognitive training application during the specified time period. In certain embodiments, method 2100 may comprise one or more steps or operations for processing (e.g., with the application server) the plurality of user activity data according to the machine learning framework to generate one or more recommendations for the second end user. In certain embodiments, the one or more recommendations may comprise recommendations for improving the measure of user engagement for the first end user. In certain embodiments, the at least one computerized adjustable element comprises a graphical indication of the quantified number of sessions of the cognitive training application for the first end user and the measure of user engagement for the first end user. In certain embodiments, the one or more graphical user interface elements comprise a graphical indication that the measure of user engagement for the first end user is below a specified threshold for the specified time period. In certain embodiments, method 2100 may comprise one or more steps or operations for configuring or modifying (e.g., with the application server) the one or more graphical user interface elements for the companion application in response to processing a second or subsequent plurality of user activity data according to the machine learning framework. In certain embodiments, method 2100 may comprise one or more steps or operations for providing (e.g., with the application server) the one or more quantitative metrics for the first end user to a third end user computing device, wherein the third end user computing device is associated with a third end user comprising a payor user.

In a non-limiting example implementation, as described in the present disclosure, the EEG can be a low-cost EEG for medical treatment validation and personalized medicine. The low-cost EEG device can be easier to use and has the potential to vastly improve the accuracy and the validity of medical applications. In this example, the platform product may be configured as an integrated device including the EEG component coupled with the cognitive platform, or as a cognitive platform that is separate from, but configured for coupling with the EEG component.

In a non-limiting example use for treatment validation, the user interacts with a cognitive platform, and the EEG is used to perform physiological measurements of the user. Any change in EEG measurements data (such as brain-waves) are monitored based on the actions of the user in interacting with the cognitive platform. The nData from the measurements using the EEG (such as brainwaves) can be collected and analyzed to detect changes in the EEG measurements. This analysis can be used to determine the types of response from the user, such as whether the user is performing according to an optimal or desired profile.

In a non-limiting example use for personalized medicine, the nData from the EEG to measurements be used to identify changes in user performance/condition that indicate that the cognitive platform treatment is having the desired effect (including to determine the type of tasks and/or CSIs that works for a given user). The analysis can be used to determine whether the cognitive platform should be caused to provide tasks and/or CSIs to enforce or diminish these user results that the EEG is detecting, by adjusting users' experience in the application.

In a non-limiting example implementation, measurements are made using a cognitive platform that is configured for coupling with a fMRI, for use for medical application validation and personalized medicine. Consumer-level fMRI devices may be used to improve the accuracy and the validity of medical applications by tracking and detecting changes in brain part stimulation.

In a non-limiting example, fMRI measurements can be used to provide measurement data of the cortical thickness and other similar measurement data. In a non-limiting example use for treatment validation, the user interacts with a cognitive platform, and the fMRI is used to measure physiological data. The user is expected to have stimulation of a particular brain part or combination of brain parts based on the actions of the user while interacting with the cognitive platform. In this example, the platform product may be configured as an integrated device including the fMRI component coupled with the cognitive platform, or as a cognitive platform that is separate from, but configured for coupling with the fMRI component. Using the application with the fMRI, measurement can be made of the stimulation of portions of the user brain, and analysis can be performed to detect changes to determining whether the user is exhibiting the desired responses.

In a non-limiting example use for personalized medicine, the fMRI can be used to collect measurement data to be used to identify the progress of the user in interacting with the cognitive platform. The analysis can be used to determine whether the cognitive platform should be caused to provide tasks and/or CSIs to enforce or diminish these user results that the fMRI is detecting, by adjusting users' experience in the application.

In any example herein, the adjustment(s) or modification(s) to, or presentments of, the type of tasks, notifications, and/or CSIs can be made in real-time.

The above-described embodiments can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

As will be appreciated by one of skill in the art, embodiments of the present disclosure may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A computer-implemented method comprising:

configuring, with a server comprising at least one processor, an instance of a first application for a first end user and an instance of a second application for a second end user;

linking, with the server, the first end user and the second end user in an application database, wherein linking the first end user and the second end user comprises enabling at least one data transfer interface between the first application and the second application;

presenting, with a first end user computing device communicably engaged with the server, the instance of the first application to the first end user, wherein the instance of the first application comprises one or more computerized stimuli or interactions configured to elicit a specified response from the first end user;

receiving, with the server, a plurality of user activity data indicative of a plurality of user-generated responses by the first end user to the one or more computerized stimuli or interactions presented during the instance of the first application;

processing, with the server, the plurality of user activity data according to at least one machine learning model configured to classify one or more stimulus-response patterns from the plurality of user activity data to generate a classified dataset comprising one or more data labels for one or more attributes of the plurality of user activity data;

storing, with the server, the classified dataset in the application database;

presenting, with a second end user computing device communicably engaged with the server, the instance of the second application to the second end user, the instance of the second application comprising a graphical user interface;

configuring or modifying, at the graphical user interface of the second application, one or more graphical user interface elements for the second application according to one or more datapoints from the classified dataset;

presenting, at the graphical user interface of the second application, the one or more graphical user interface elements to the second end user, wherein the one or more graphical user interface elements comprise at least one computerized adjustable element configured to provide one or more quantitative metrics for the first end user according to the classified dataset, wherein the at least one computerized adjustable element comprises a graphical indication to the second end user that a degree of effort for the first end user is at or below a target threshold based on an output of the at least one machine learning model;

processing, with the server, the plurality of user activity data to generate one or more recommendations for improving the degree of effort for the first end user in a subsequent instance of the first application;

presenting, at the graphical user interface of the second application, the one or more recommendations to the second end user;

receiving, via the graphical user interface of the second application, at least one user-generated input from the second end user in accordance with the one or more recommendations;

processing, with the server, the at least one user-generated input from the second end user in response to the one or more recommendations; and configuring or modifying, with the server, one or more subsequent computerized stimuli or interactions for the subsequent instance of the first application to improve the degree of effort for the first end user in response to the processing of the at least one user-generated input from the second end user in accordance with the one or more recommendations.

2. The computer-implemented method of claim 1 wherein the one or more quantitative metrics comprise a quantified number of sessions of the first application for the first end user for a specified time period.

3. The computer-implemented method of claim 2 wherein the one or more quantitative metrics comprise a measure of user engagement for the first end user during the quantified number of sessions.

4. The computer-implemented method of claim 3 wherein the at least one computerized adjustable element is config- ured to indicate an amount of time the first end user engaged with the instance of the first application during the specified time period.

5. The computer-implemented method of claim 3 wherein the one or more graphical user interface elements comprise a graphical indication that the measure of user engagement for the first end user is below a specified threshold for the specified time period.

6. The computer-implemented method of claim 1 further comprising configuring or modifying, with the server, the one or more graphical user interface elements for the second application in response to processing a second or subsequent plurality of user activity data.

7. The computer-implemented method of claim 1 further comprising providing, with the server, the one or more quantitative metrics for the first end user to a third end user computing device, wherein the third end user computing device is associated with a third end user comprising a payor user.

8. A computer-implemented system comprising:
a first end user computing device;
a second end user computing device; and
a server communicably engaged with the first end user computing device and the second end user computing device, the server comprising at least one processor and a non-transitory computer readable medium encoded with one or more processor-executable instructions thereon that, when executed, command the at least one processor to perform one or more operations, the one or more operations comprising:
configuring an instance of a first application for a first end user and an instance of a second application for a second end user;
linking the first end user and the second end user in an application database, wherein linking the first end user and the second end user comprises enabling at least one data transfer interface between the first application and the second application;
presenting the instance of the first application to the first end user, wherein the instance of the first application comprises one or more computerized stimuli or inter- actions configured to elicit a specified response from the first end user;
receiving a plurality of user activity data indicative of a plurality of user-generated responses by the first end user to the one or more computerized stimuli or inter- actions presented during the instance of the first appli- cation;
processing the plurality of user activity data according to at least one machine learning model configured to classify one or more stimulus-response patterns from the plurality of user activity data to generate a classified dataset comprising one or more data labels for one or more attributes of the plurality of user activity data;
storing the classified dataset in the application database;
presenting the instance of the second application for the first application to the second end user, the instance of the second application comprising a graphical user interface;
configuring or modifying, at the graphical user interface of the second application, one or more graphical user interface elements for the second application according to one or more datapoints from the classified dataset;
presenting, with the instance of the second application, the one or more graphical user interface elements to the second end user, wherein the one or more graphical user interface elements comprise at least one comput- erized adjustable element configured to provide one or more quantitative metrics for the first end user accord- ing to the classified dataset,
wherein the at least one computerized adjustable element comprises a graphical indication to the second end user that a degree of effort for the first end user is at or below a target threshold based on an output of the at least one machine learning model;
processing the plurality of user activity data according to the machine learning framework to generate one or more recommendations for improving the degree of effort for the first end user in a subsequent instance of the first application;
presenting, at the graphical user interface of the second application, the one or more recommendations to the second end user;
receiving, via the graphical user interface of the second application, at least one user-generated input from the second end user in accordance with the one or more recommendations;
processing the received at least one user-generated input from the second end user in accordance with the one or more recommendations; and
configuring or modifying one or more subsequent com- puterized stimuli or interactions for the subsequent instance of the first application to improve the degree of effort for the first end user in response to the processing of the at least one user-generated input from the second end user in accordance with the one or more recom- mendations.

9. The computer-implemented system of claim 8 wherein the one or more quantitative metrics comprise a quantified number of sessions of the first application for the first end user for a specified time period.

10. The computer-implemented system of claim 9 wherein the one or more quantitative metrics comprise a measure of user engagement for the first end user during the quantified number of sessions.

11. The computer-implemented system of claim 10 wherein the at least one computerized adjustable element is configured to indicate an amount of time the first end user engaged with the instance of the first application during the specified time period.

12. The computer-implemented system of claim 10 wherein the one or more graphical user interface elements comprise a graphical indication that the measure of user engagement for the first end user is below a specified threshold for the specified time period.

13. The computer-implemented system of claim 8 wherein the one or more operations further comprise opera- tions for configuring or modifying the one or more graphical user interface elements for the second application in response to processing a second or subsequent plurality of user activity data.

14. The computer-implemented system of claim 8 wherein the one or more operations further comprise operations for providing the one or more quantitative metrics for the first end user to a third end user computing device, wherein the third end user computing device is associated with a third end user comprising a payor user.

15. The computer-implemented system of claim 13 wherein the one or more graphical user interface elements for the second application are configured or modified in real-time in response to processing the second or subsequent plurality of user activity data.

16. A non-transitory computer-readable medium with one or more processor-executable instructions stored thereon that, when executed, command one or more processors to perform one or more operations, the one or more operations comprising:

configuring an instance of a first application for a first end user and an instance of a second application for a second end user;

linking the first end user and the second end user in an application database, wherein linking the first end user and the second end user comprises enabling at least one data transfer interface between the first application and the second application;

presenting the instance of the first application to the first end user, wherein the instance of the first application comprises one or more computerized stimuli or interactions configured to elicit a specified response from the first end user;

receiving a plurality of user activity data comprising a plurality of input sensor data indicative of a plurality of user-generated responses by the first end user to the one or more computerized stimuli or interactions presented during the instance of the first application;

processing the plurality of user activity data according to at least one machine learning model configured to classify one or more stimulus-response patterns from the plurality of user activity data to generate a classified dataset comprising one or more data labels for one or more attributes of the plurality of user activity data;

storing the classified dataset in the application database;

presenting the instance of the second application for the first application to the second end user, the instance of the second application comprising a graphical user interface;

configuring or modifying, at the graphical user interface of the second application, one or more graphical user interface elements for the second application according to one or more datapoints from the classified dataset;

presenting, with the instance of the second application, the one or more graphical user interface elements to the second end user, wherein the one or more graphical user interface elements comprise at least one computerized adjustable element, wherein the at least one computerized adjustable element comprises a graphical indication to the second end user that a degree of effort for the first end user is at or below a target threshold based on an output of the at least one machine learning model;

processing the plurality of user activity data to generate one or more recommendations for improving the degree of effort for the first end user in a subsequent instance of the first application;

presenting, at the graphical user interface of the second application, the one or more recommendations to the second end user;

receiving, via the graphical user interface of the second application, at least one user-generated input from the second end user in accordance with the one or more recommendations;

processing the received at least one user-generated input from the second end user in accordance with the one or more recommendations; and configuring or modifying one or more subsequent computerized stimuli or interactions for the subsequent instance of the first application to improve the degree of effort for the first end user in response to the processing of the at least one user-generated input from the second end user in accordance with the one or more recommendations.

\* \* \* \* \*